United States Patent
Calman et al.

(10) Patent No.: US 8,582,850 B2
(45) Date of Patent: Nov. 12, 2013

(54) PROVIDING INFORMATION REGARDING MEDICAL CONDITIONS

(75) Inventors: Matthew A. Calman, Charlotte, NC (US); Erik Stephen Ross, Charlotte, NC (US)

(73) Assignee: Bank of America Corporation, Charlotte, NC (US)

( * ) Notice: Subject to any disclaimer, the term of this patent is extended or adjusted under 35 U.S.C. 154(b) by 131 days.

(21) Appl. No.: 13/342,060

(22) Filed: Jan. 1, 2012

(65) Prior Publication Data
US 2012/0230557 A1     Sep. 13, 2012

Related U.S. Application Data

(60) Provisional application No. 61/450,213, filed on Mar. 8, 2011, provisional application No. 61/508,985, filed on Jul. 18, 2011.

(51) Int. Cl.
*G06K 9/00* (2006.01)
*H04M 1/00* (2006.01)

(52) U.S. Cl.
USPC ............................ 382/128; 382/206; 455/555

(58) Field of Classification Search
USPC ......... 382/100, 103, 113, 128–134, 155, 162, 382/168, 173, 181, 203, 206, 209, 224, 232, 382/254, 274, 276, 291, 305; 455/90.1, 455/555; 707/769, 10; 705/44
See application file for complete search history.

(56) References Cited

U.S. PATENT DOCUMENTS

| | | | |
|---|---|---|---|
| 7,016,532 B2 | 3/2006 | Boncyk et al. | |
| 7,155,228 B2 | 12/2006 | Rappaport et al. | |
| 7,403,652 B2 | 7/2008 | Boncyk et al. | |
| 7,412,081 B2 | 8/2008 | Doi | |
| 7,424,303 B2 | 9/2008 | Al-Sarawi | |
| 7,477,780 B2 | 1/2009 | Boncyk et al. | |
| 7,526,280 B2 | 4/2009 | Jung et al. | |
| 7,564,469 B2 | 7/2009 | Cohen | |
| 7,565,008 B2 | 7/2009 | Boncyk et al. | |

(Continued)

OTHER PUBLICATIONS

International Searching Authority. PCT International Search Report and Written Opinion dated Jun. 8, 2012. PCT International Application No. PCT/US2012/027912. Name of Applicant: Bank of America Corporation. English Language. 12 pages.

(Continued)

*Primary Examiner* — Seyed Azarian
(74) *Attorney, Agent, or Firm* — Michael A. Springs; Moore and Van Allen, PLLC; Patrick B. Horne

(57) ABSTRACT

Systems, methods, and computer program products are provided for using real-time video analysis and AR or the like to assist the user of mobile devices with commerce activities. Through the use of real-time vision object recognition medical conditions can be recognized in the real-time video stream and can be matched to medical condition related information regarding the medical condition and can also be matched to one or more targeted offers for products related to the medical condition. The medical condition related information may be presenting to the user of the mobile device in conjunction with display of the associated medical condition in a live video stream. Further, in some embodiments, a product can be recognized as products related to a previously recognized medical condition and indicators associated with the recognized products can be presented with the real-time video stream.

28 Claims, 8 Drawing Sheets

(56) References Cited

U.S. PATENT DOCUMENTS

| | | | |
|---|---|---|---|
| 7,680,324 B2 | 3/2010 | Boncyk et al. | |
| 7,775,437 B2 | 8/2010 | Cohen | |
| 7,792,738 B2 | 9/2010 | Channell | |
| 7,881,529 B2 | 2/2011 | Boncyk et al. | |
| 7,899,243 B2 | 3/2011 | Boncyk et al. | |
| 7,899,252 B2* | 3/2011 | Boncyk et al. | 382/181 |
| 8,138,930 B1 | 3/2012 | Heath | |
| 8,392,450 B2* | 3/2013 | Blanchflower et al. | 707/769 |
| 2003/0064705 A1 | 4/2003 | Desiderio | |
| 2004/0021584 A1 | 2/2004 | Hartz, Jr. et al. | |
| 2004/0024709 A1 | 2/2004 | Yu et al. | |
| 2006/0100951 A1 | 5/2006 | Mylet | |
| 2007/0140595 A1 | 6/2007 | Taylor | |
| 2008/0040278 A1* | 2/2008 | DeWitt | 705/44 |
| 2008/0214210 A1 | 9/2008 | Rasanen et al. | |
| 2008/0268876 A1 | 10/2008 | Gelfand et al. | |
| 2009/0094125 A1 | 4/2009 | Killian et al. | |
| 2009/0102859 A1 | 4/2009 | Athsani et al. | |
| 2009/0140839 A1 | 6/2009 | Bishop et al. | |
| 2009/0144164 A1 | 6/2009 | Wane et al. | |
| 2009/0171850 A1 | 7/2009 | Yuval | |
| 2009/0182748 A1* | 7/2009 | Walker | 707/10 |
| 2009/0204511 A1 | 8/2009 | Tsang | |
| 2009/0250515 A1 | 10/2009 | Todd et al. | |
| 2010/0130226 A1 | 5/2010 | Arrasvuori et al. | |
| 2010/0185529 A1 | 7/2010 | Chesnut et al. | |
| 2010/0250581 A1 | 9/2010 | Chau | |
| 2010/0255795 A1* | 10/2010 | Rubinsky et al. | 455/90.1 |
| 2011/0022540 A1 | 1/2011 | Stern et al. | |
| 2011/0034176 A1 | 2/2011 | Lord et al. | |
| 2011/0119155 A1 | 5/2011 | Hammad et al. | |
| 2011/0202466 A1 | 8/2011 | Carter | |

OTHER PUBLICATIONS

International Searching Authority. PCT International Search Report and Written Opinion dated Jun. 14, 2012. PCT International Application No. PCT/US12/27892. Name of Applicant: Bank of America Corporation. English Language. 19 pages.

International Searching Authority. PCT International Search Report and Written Opinion dated Sep. 24, 2012. PCT International Application No. PCT/US12/48697. Name of Applicant: Bank of America Corporation. English Language. 14 pages.

International Search Report and Written Opinion for International Application No. PCT/US12/27890 dated Feb. 5, 2013.

International Searching Authority. PCT International Search Report and Written Opinion dated May 28, 2012. PCT International Application No. PCT/US12/28036. Name of Applicant: Bank of America Corporation. English Language. 11 pages.

International Searching Authority. PCT International Search Report and Written Opinion dated May 22, 2012. PCT International Application No. PCT/US12/28008. Name of Applicant: Bank of America Corporation. English Language. 13 pages.

International Preliminary Report on Patentability and Written Opinion dated Sep. 10, 2013 for International Application No. PCT/US2012/028036.

International Preliminary Report on Patentability and Written Opinion dated Sep. 10, 2013 for International Application No. PCT/US2012/027892.

International Preliminary Report on Patentability and Written Opinion dated Sep. 10, 2013 for International Application No. PCT/US2012/028008.

International Preliminary Report on Patentability and Written Opinion dated Sep. 10, 2013 for International Application No. PCT/US2012/027912.

* cited by examiner

PROVIDING INFORMATION REGARDING MEDICAL CONDITIONS

CROSS-REFERENCE TO RELATED APPLICATIONS

This application claims priority to U.S. Provisional Patent Application Ser. No. 61/450,213, filed Mar. 8, 2011, entitled "Real-Time Video Image Analysis Applications for Commerce Activity," and U.S. Provisional Patent Application Ser. No. 61/508,985, filed Jul. 18, 2011, entitled "Providing Information Regarding Medical Conditions," the entirety of each of which is incorporated herein by reference.

FIELD

In general, embodiments herein disclosed relate to commerce and, more specifically, providing medical condition related information and/or product indications and/or offers associated with medical conditions on a mobile communication device in conjunction with a live video stream.

BACKGROUND

Modern handheld mobile devices, such as smart phones or the like, combine multiple technologies to provide the user with a vast array of capabilities. For example, many smart phones are equipped with significant processing power, sophisticated multi-tasking operating systems, and high-bandwidth Internet connection capabilities. Moreover, such devices often have addition features that are becoming increasing more common and standardized features. Such features include, but are not limited to, location-determining devices, such as Global Positioning System (GPS) devices; sensor devices, such as accelerometers; and high-resolution video cameras.

As the hardware capabilities of such mobile devices have increased, so too have the applications (i.e., software) that rely on the hardware advances. One such example of innovative software is a category known as augmented reality (AR), or more generally referred to as mediated reality. One such example of an AR application platform is Layar, available from Layar, Amsterdam, the Netherlands.

The Layar platform technology analyzes location data, compass direction data, and the like in combination with information related to the objects, locations or the like in the video stream to create browse-able "hot-spots" or "tags" that are superimposed on the mobile device display, resulting in an experience described as "reality browsing".

Therefore, a need exists to further the capabilities of mobile communication devices and, in particular leverage augmented-reality type analysis to provide mobile device user's with greater access to information.

SUMMARY

The following presents a simplified summary of one or more embodiments in order to provide a basic understanding of such embodiments. This summary is not an extensive overview of all contemplated embodiments, and is intended to neither identify key or critical elements of all embodiments nor delineate the scope of any or all embodiments. Its sole purpose is to present some concepts of one or more embodiments in a simplified form as a prelude to the more detailed description that is presented later.

Methods, apparatus systems and computer program products are described herein that provide for using real-time video analysis and AR or the like to assist the user of mobile devices with accessing medical condition related information and/or product offers associated with recognized medical conditions and the like. Through the use of real-time vision object recognition, medical conditions can be recognized in the video stream and can be matched to data associated with the treatment of the medical conditions. In some embodiments, products are identified and medical condition related information indicators are presented proximate a product determined to be associated with treatment of a previously identified medical condition.

According to embodiments of the invention, a method provides medical condition related information. The method includes identifying, via a computing device processor, which objects in an image captured on a mobile communication device correspond to a medical condition, determining, via a computing device processor, which of one or more medical conditions identified in the image video stream have associated medical condition related information, and presenting, via a display of the image on the mobile communication device, one or more medical condition related information indicators, each medical condition related information indicator presented proximate a location of the one or more medical conditions determined to have associated medical condition related information.

In some embodiments, identifying a medical condition comprises identifying one or more images in a video stream captured on a mobile communication device that correspond to one or more medical conditions. In some embodiments, identifying a medical condition comprises identifying one or more objects in a still image captured on a mobile communication device that corresponds to one or more medical conditions. In some embodiments, identifying a medical condition comprises identifying one or more medical conditions based at least in part on global positioning system information associated with the mobile communication device or other information indicating a location of the mobile communication device. In some embodiments, the medical condition related information comprises information related to the medical condition comprising information regarding proper treatment of the medical condition. In some embodiments, determining which of the identified medical conditions have associated medical condition related information comprises comparing the identified medical conditions to a database listing of medical conditions currently associated with medical condition related information.

According to embodiments of the invention, an apparatus for providing medical condition related information includes a computing platform having a processor and a memory in communication with the processor. The apparatus also includes image capture logic stored in the memory, executable by the processor and configured to capture an image, medical condition identification logic stored in the memory, executable by the processor and configured to identify which objects in the image captured by a mobile communication device correspond to a medical condition, medical condition related information logic stored in the memory, executable by the processor and configured to determine whether the identified medical condition has associated medical condition related information, and medical condition related information presentation logic stored in the memory, executable by the processor and configured to present, on a display of the mobile communication device, one or more medical condition related information indicators, each medical condition related information indicator presented proximate a location of the medical condition determined to have associated medical condition related information.

In some embodiments, the medical condition identification logic is configured to identify one or more images in a video stream captured on a mobile communication device that correspond to one or more medical conditions. In some embodiments, the medical condition identification logic is configured to identify one or more objects in a still image captured on a mobile communication device that corresponds to one or more medical conditions. In some embodiments, the medical condition identification logic is configured to identify one or more medical conditions based at least in part on global positioning system information associated with the mobile communication device or other information indicating a location of the mobile communication device. In some embodiments, the medical condition related information comprises information related to the medical condition comprising information regarding proper treatment of the medical condition. In some embodiments, the medical condition related information logic is configured to determine which of the identified medical conditions have associated medical condition related information comprises comparing the identified medical conditions to a database listing of medical conditions currently associated with medical condition related information.

According to embodiments of the invention, a computer program product includes a non-transitory computer-readable medium having computer-executable instructions for providing health related information. The instructions include instructions for identifying which objects in an image captured on a mobile communication device correspond to a medical condition, instructions for determining which of one or more medical conditions identified in the image have associated medical condition related information, and instructions for presenting one or more medical condition related information indicators with an image displayed on the mobile communication device, each medical condition related information indicator presented proximate a location of the one or more determined medical conditions.

According to embodiments of the invention, a method for providing medical condition related information includes identifying, via a server in communication with a mobile communication device, which objects in an image captured on a mobile communication device correspond to a medical condition, determining, via the server, which of one or more medical conditions identified in the image have associated medical condition related information, and communicating instructions to the mobile communication device, via the server, for presenting a display of the image on the mobile communication device, one or more medical condition related information indicators, each medical condition related information indicator presented proximate a location of the one or more medical conditions determined to have associated medical condition related information.

In some embodiments, identifying a medical condition comprises identifying one or more images in a video stream captured on a mobile communication device that correspond to one or more medical conditions. In some embodiments, identifying a medical condition comprises identifying one or more objects in a still image captured on a mobile communication device that corresponds to one or more medical conditions. In some embodiments, identifying a medical condition comprises identifying one or more medical conditions based at least in part on global positioning system information associated with the mobile communication device or other information indicating a location of the mobile communication device. In some embodiments, the medical condition related information comprises information related to the medical condition comprising information regarding proper treatment of the medical condition. In some embodiments, determining which of the identified medical conditions have associated medical condition related information comprises comparing the identified medical conditions to a database listing of medical conditions currently associated with medical condition related information.

According to embodiments of the invention, an apparatus for providing medical condition related information includes a server having a processor and a memory in communication with the processor. The apparatus also includes communication logic stored in the memory, executable by the processor and configured to receive data from a mobile communication device, the data corresponding to one or more objects in an image captured by the mobile communication device; medical condition identification logic stored in the memory, executable by the processor and configured to identify which objects in the image captured by the mobile communication device correspond to a medical condition; medical condition related information logic stored in the memory, executable by the processor and configured to determine whether the identified medical condition has associated medical condition related information; and medical condition related information presentation logic stored in the memory, executable by the processor and configured to communicate instructions for presenting, on a display of the mobile communication device, one or more medical condition related information indicators, each medical condition related information indicator presented proximate a location of the medical condition determined to have associated medical condition related information.

In some embodiments, the medical condition identification logic is configured to identify one or more images in a video stream captured on a mobile communication device that correspond to one or more medical conditions. In some embodiments, the medical condition identification logic is configured to identify one or more objects in a still image captured on a mobile communication device that corresponds to one or more medical conditions. In some embodiments, the medical condition identification logic is configured to identify one or more medical conditions based at least in part on global positioning system information associated with the mobile communication device or other information indicating a location of the mobile communication device. In some embodiments, the medical condition related information comprises information related to the medical condition comprising information regarding proper treatment of the medical condition. In some embodiments, the medical condition related information logic is configured to compare the identified medical conditions to a database listing of medical conditions currently associated with medical condition related information.

According to embodiments of the invention, a computer program product includes a non-transitory computer-readable medium having computer-executable instructions for execution on a server in communication with a mobile communication device, the instructions for providing medical condition related information. The instructions include instructions for identifying which objects in an image captured on a mobile communication device correspond to a medical condition; instructions for determining which of one or more medical conditions identified in the image have associated medical condition related information; and instructions for communicating instructions to the mobile communication device for presenting one or more medical condition related information indicators with the image displayed on the mobile communication device, each medical condition related information indicator presented proximate a location of the one or more determined medical conditions.

According to embodiments of the invention, a method for providing medical condition information includes identifying, via a computing device processor, which objects in an image captured on a mobile communication device correspond to a product; determining, via a computing device processor, which of one or more products identified in the image are associated with treatment of a previously identified medical condition; and presenting, via a display of the live video stream on the mobile communication device, one or more medical condition indicators, each medical condition indicator presented proximate a location of the one or more products determined to be associated with treatment of the previously identified medical condition.

In some embodiments, the medical condition related information comprises at least one of nutrition information, caloric information, medical indication information, proper medicinal treatment information, or financial impact information. In some embodiments, determining which of the identified products have associated medical condition related information comprises comparing the identified products to a database listing of products currently associated with medical condition related information. In some embodiments, the method also includes storing information related to at least one medical or health need or want of a social network member of a user of the mobile communication device; determining whether any of the identified products meet the health need or want of the social network member; and presenting at least one health related information indicator indicating that at least one identified product meets the health need or want of the social network member. In some embodiments, the method also includes storing information related to at least one medical or health characteristic of a user of the mobile communication device; determining whether any of the identified products effect the health characteristic of the user; and presenting at least one health related information indicator indicating that at least one identified product effects the health characteristic of the user.

According to embodiments of the invention, an apparatus for providing medical condition information includes a computing platform having a processor and a memory in communication with the processor. The apparatus also includes image capture logic stored in the memory, executable by the processor and configured to capture an image, product identification logic stored in the memory, executable by the processor and configured to identify which objects in the image captured by a mobile communication device correspond to a product, medical condition related information logic stored in the memory, executable by the processor and configured to determine whether the identified product is associated with treatment of a previously identified medical condition, and medical condition related information presentation logic stored in the memory, executable by the processor and configured to present, on a display of the mobile communication device, one or more medical condition related information indicators, each medical condition related information indicator presented proximate a location of the product determined to be associated with treatment of the previously identified medical condition.

To the accomplishment of the foregoing and related ends, the one or more embodiments comprise the features hereinafter fully described and particularly pointed out in the claims. The following description and the annexed drawings set forth in detail certain illustrative features of the one or more embodiments. These features are indicative, however, of but a few of the various ways in which the principles of various embodiments may be employed, and this description is intended to include all such embodiments and their equivalents.

BRIEF DESCRIPTION OF THE DRAWINGS

Figure 1:
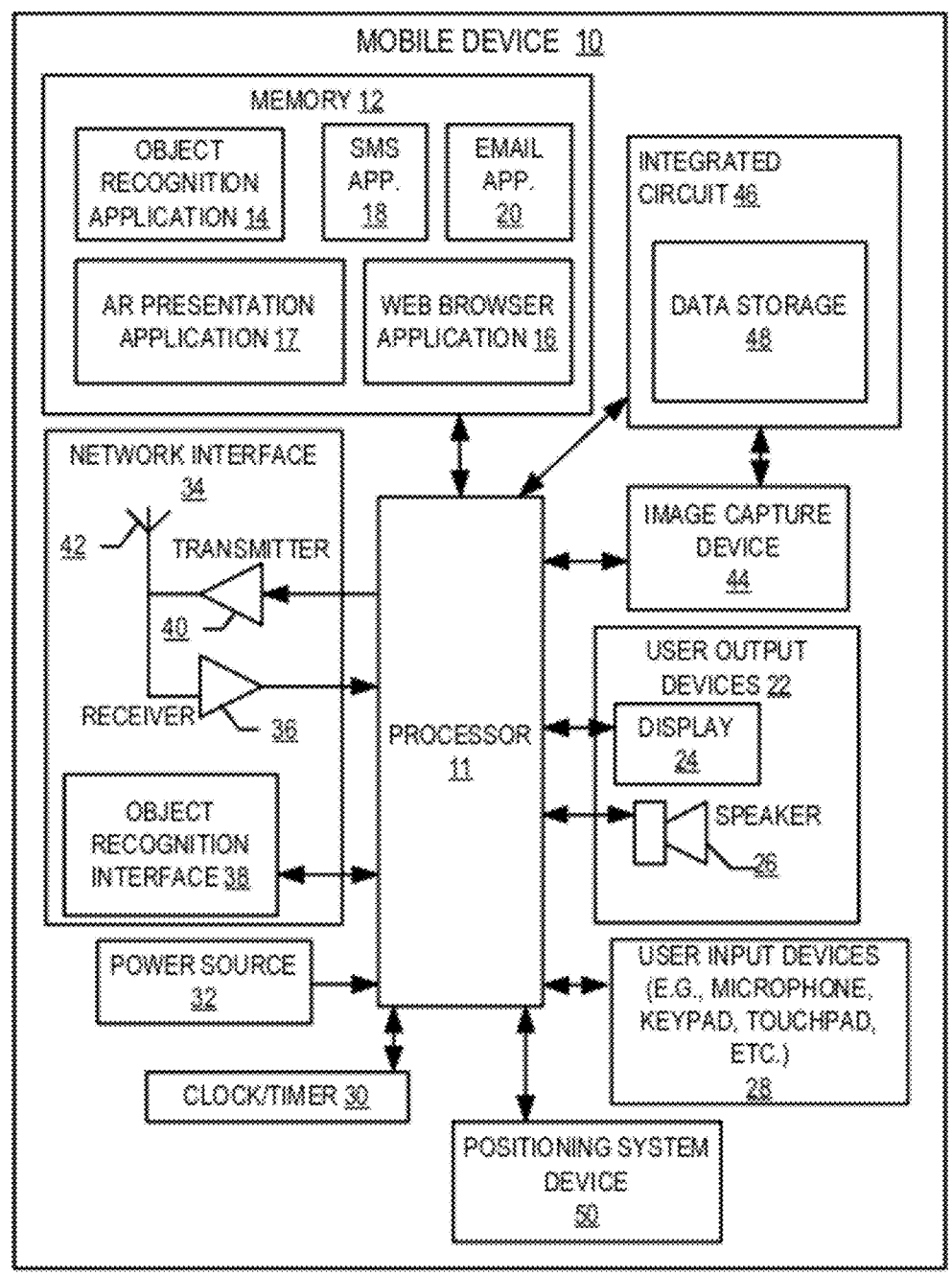
Figure 2:
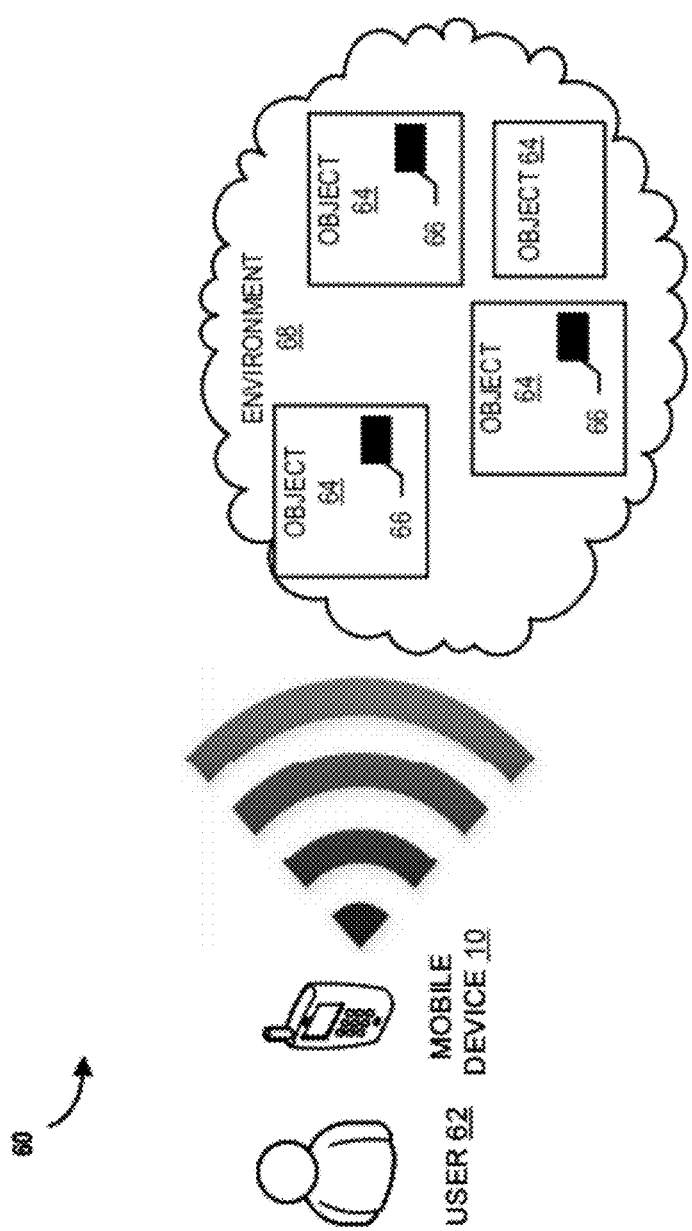
Figure 3:
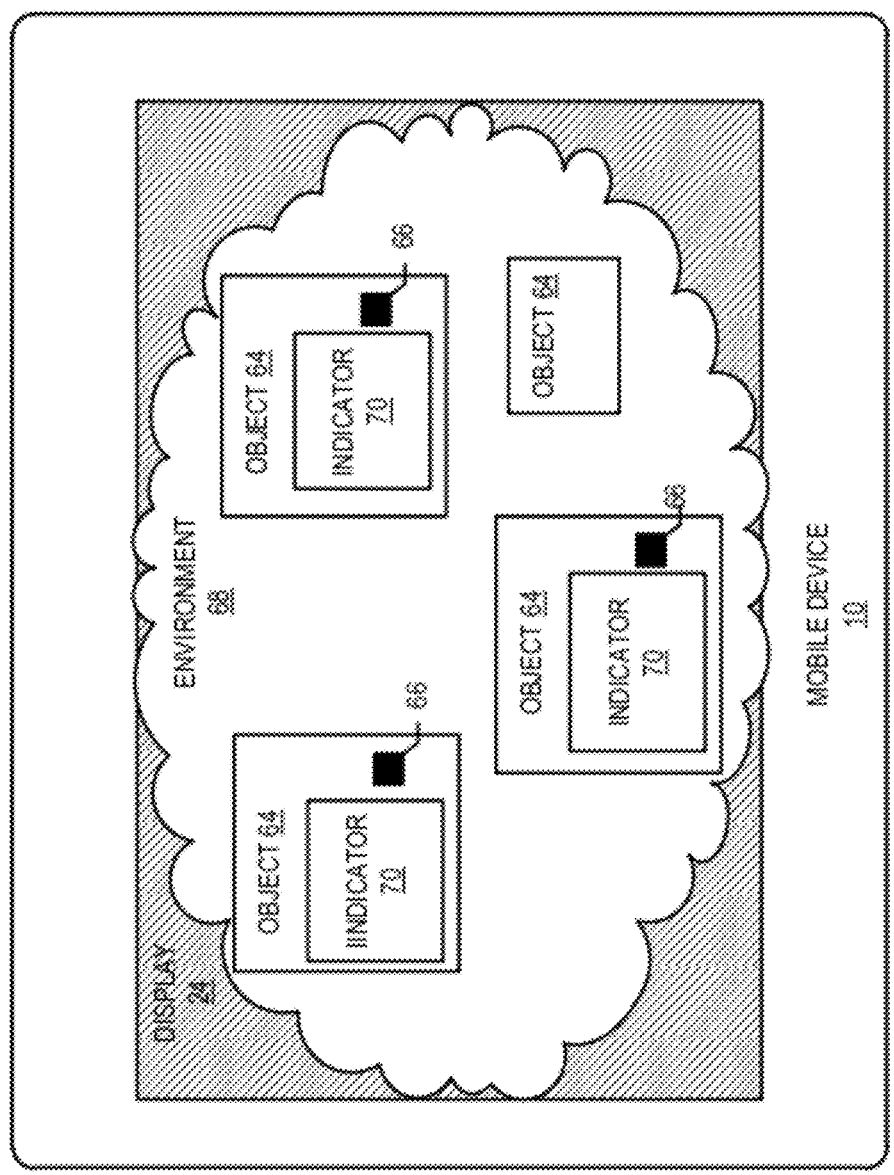
Figure 4:
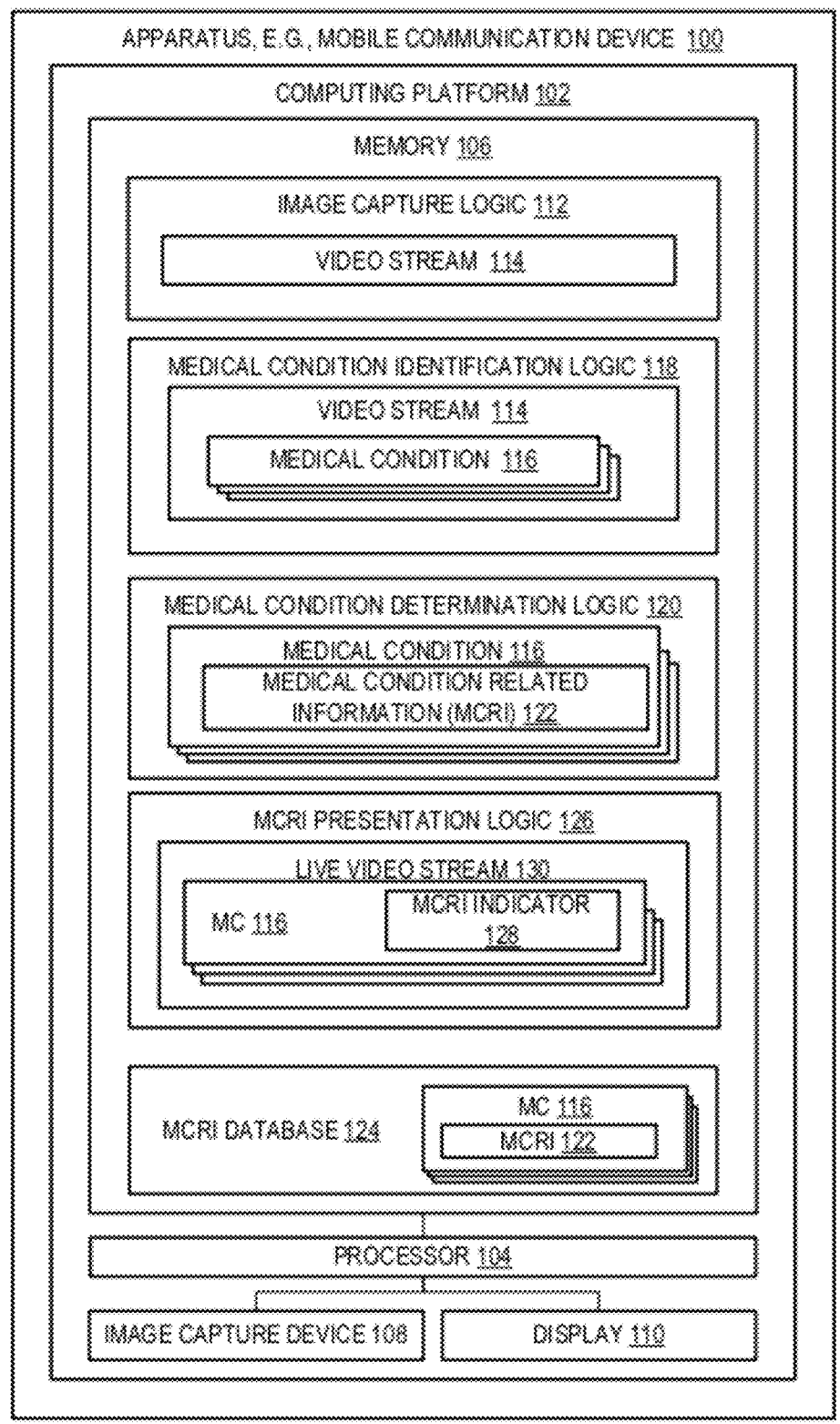
Figure 5:
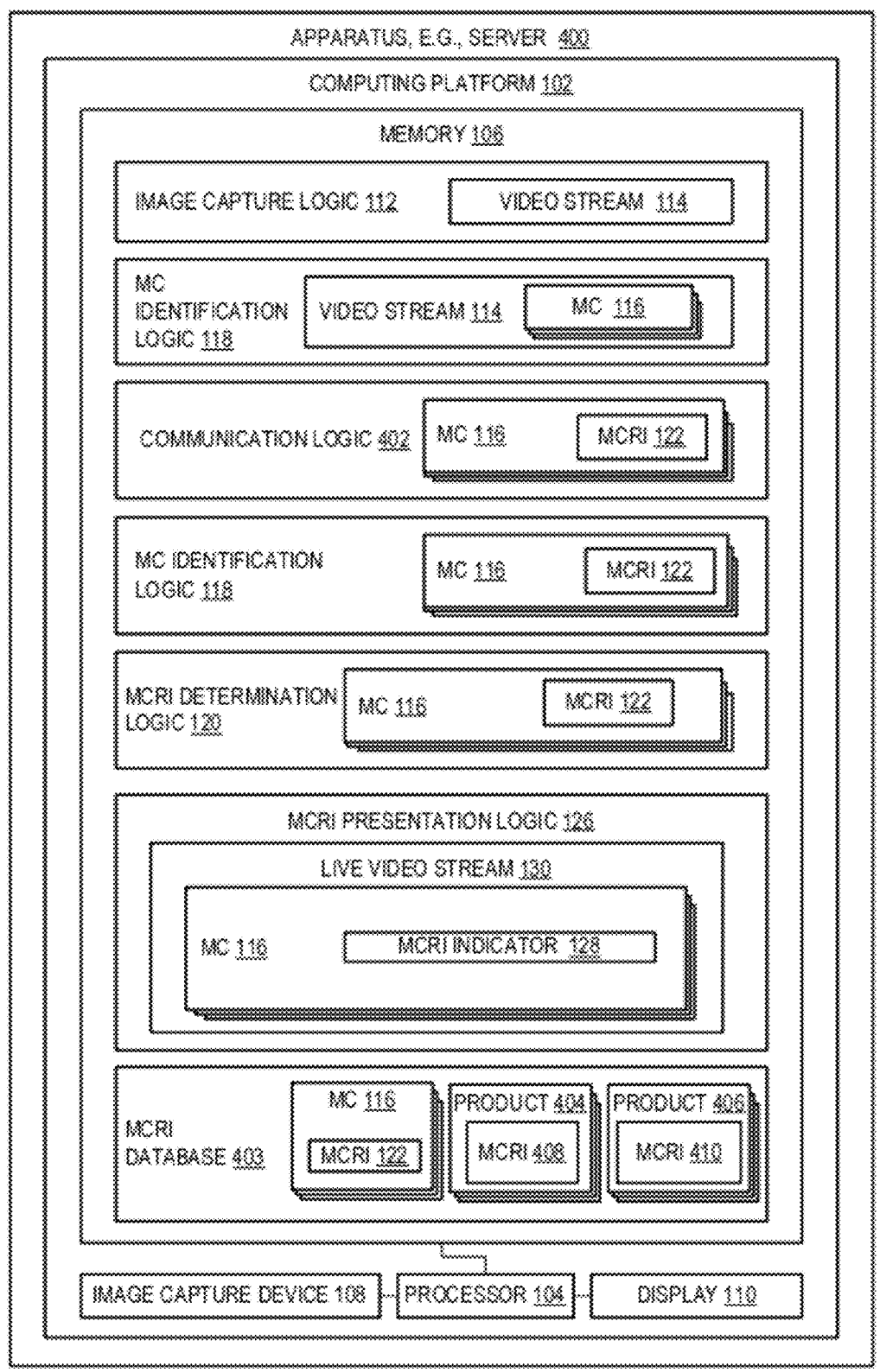
Figure 6:
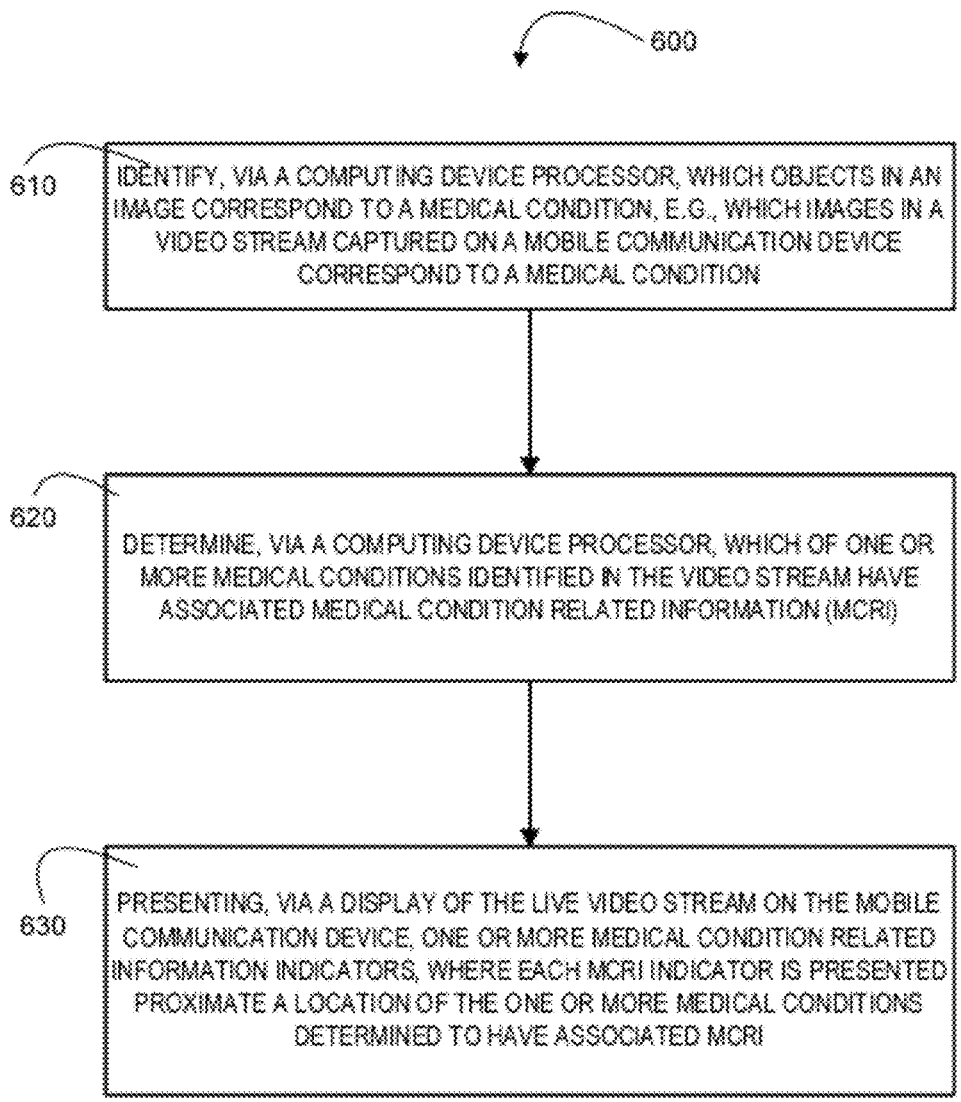
Figure 7:
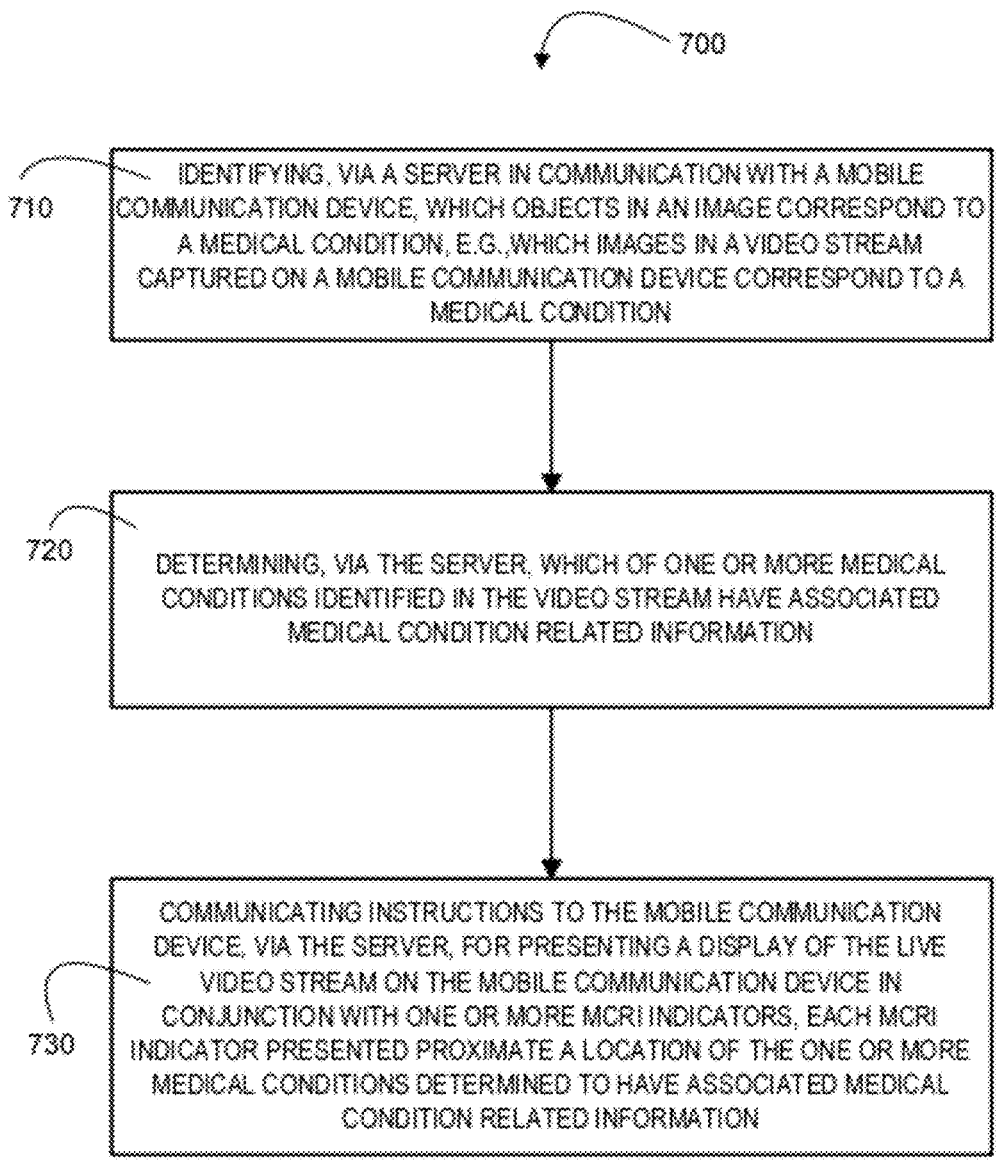
Figure 8:
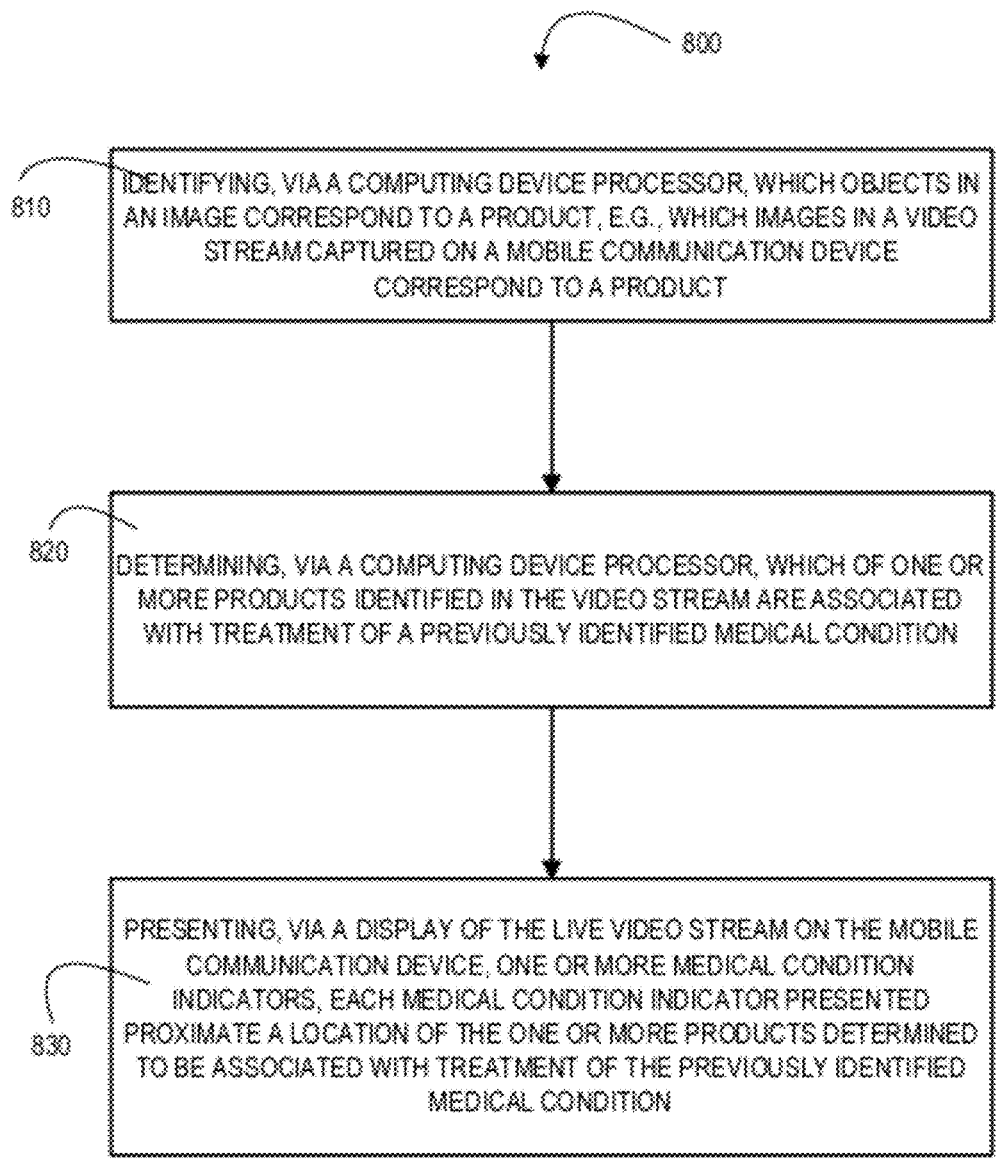

Having thus described embodiments of the invention in general terms, reference will now be made to the accompanying drawings, which are not necessarily drawn to scale, and wherein:

FIG. 1 is a block diagram illustrating a mobile device, in accordance with an embodiment of the invention;

FIG. 2 is a block diagram illustrating an AR environment, in accordance with an embodiment of the invention;

FIG. 3 is a block diagram illustrating a mobile device, in accordance with an embodiment of the invention;

FIG. 4 is a block diagram of an apparatus, such as a mobile communication device, configured to present medical condition related information in conjunction with display of the medical condition in a live video stream on a mobile communication device, in accordance with embodiment of the present invention;

FIG. 5 is an additional block diagram of an apparatus, such as a server, configured to communicate instructions configured to initiate display of medical condition related information on a mobile communication device in conjunction with display of the medical condition in a live video stream on a mobile communication device, in accordance with embodiment of the present invention;

FIG. 6 is a flow diagram illustrating a method for presenting MCRI indicators in conjunction with display of the medical condition in a live video stream on a mobile communication device, in accordance with embodiments of the present invention;

FIG. 7 is a flow diagram illustrating another method for presenting MCRI indicators in conjunction with display of the medical condition in a live video stream on a mobile communication device, in accordance with embodiments of the present invention; and FIG. 8 is a flow diagram illustrating a method for presenting MCRI indicators in conjunction with display of a product associated with treatment of a previously identified medical condition, in accordance with embodiments of the present invention.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. In the following description, for purposes of explanation, numerous specific details are set forth in order to provide a thorough understanding of one or more embodiments. It may be evident; however, that such embodiment(s) may be practiced without these specific details. Like numbers refer to like elements throughout.

Various embodiments or features will be presented in terms of systems that may include a number of devices, components, modules, and the like. It is to be understood and appreciated that the various systems may include additional devices, components, modules, etc. and/or may not include all of the devices, components, modules etc. discussed in connection with the figures. A combination of these approaches may also be used.

The steps and/or actions of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some embodiments, the processor and the storage medium may reside in an Application Specific Integrated Circuit (ASIC). In the alternative, the processor and the storage medium may reside as discrete components in a computing device. Additionally, in some embodiments, the events and/or actions of a method or algorithm may reside as one or any combination or set of codes and/or instructions on a machine-readable medium and/or computer-readable medium, which may be incorporated into a computer program product.

In one or more embodiments, the functions described may be implemented in hardware, software, firmware, or any combination thereof. If implemented in software, the functions may be stored or transmitted as one or more instructions or code on a computer-readable medium. Computer-readable media includes both computer storage media and communication media including any medium that facilitates transfer of a computer program from one place to another. A storage medium may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures, and that can be accessed by a computer. Also, any connection may be termed a computer-readable medium. For example, if software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. "Disk" and "disc", as used herein, include compact disc (CD), laser disc, optical disc, digital versatile disc (DVD), floppy disk and blu-ray disc where disks usually reproduce data magnetically, while discs usually reproduce data optically with lasers. Combinations of the above should also be included within the scope of computer-readable media.

Thus, methods, systems, computer programs and the like are herein disclosed that provide for presenting medical condition related information on mobile communication devices in conjunction with presentation of a medical condition and/or a product associated with treatment of a previously identified medical condition in a live video stream.

FIG. 1 illustrates an embodiment of a mobile device 10 that may be configured to execute object recognition and Augmented Reality (AR) functionality, in accordance with specific embodiments of the present invention. A "mobile device" 10 may be any mobile communication device, such as a cellular telecommunications device (i.e., a cell phone or mobile phone), personal digital assistant (PDA), a mobile Internet accessing device, or other mobile device including, but not limited to portable digital assistants (PDAs), pagers, mobile televisions, gaming devices, laptop computers, cameras, video recorders, audio/video player, radio, GPS devices, any combination of the aforementioned, or the like.

The mobile device 10 may generally include a processor 11 communicably coupled to such devices as a memory 12, user output devices 22, user input devices 28, a network interface 34, a power source 32, a clock or other timer 30, an image capture device 44, a positioning system device 50 (e.g., a Global Positioning System (GPS) device), one or more integrated circuits 46, etc.

In some embodiments, the mobile device and/or the server access one or more databases or data stores (not shown in FIG. 1) to search for and/or retrieve information related to the object and/or marker. In some embodiments, the mobile device and/or the server access one or more data stores local to the mobile device and/or server and in other embodiments, the mobile device and/or server access data stores remote to the mobile device and/or server. In some embodiments, the mobile device and/or server access both a memory and/or data store local to the mobile device and/or server as well as a data store remote from the mobile device and/or server The processor 11, and other processors described herein, may generally include circuitry for implementing communication and/or logic functions of the mobile device 10. For example, the processor 11 may include a digital signal processor device, a microprocessor device, and various analog to digital converters, digital to analog converters, and/or other support circuits. Control and signal processing functions of the mobile device 10 may be allocated between these devices according to their respective capabilities. The processor 11 thus may also include the functionality to encode and interleave messages and data prior to modulation and transmission. The processor 11 may additionally include an internal data modem. Further, the processor 11 may include functionality to operate one or more software programs or applications, which may be stored in the memory 12. For example, the processor 11 may be capable of operating a connectivity program, such as a web browser application 16. The web browser application 16 may then allow the mobile device 10 to transmit and receive web content, such as, for example, location-based content and/or other web page content, according to a Wireless Application Protocol (WAP), Hypertext Transfer Protocol (HTTP), and/or the like.

The processor 11 may also be capable of operating applications, such as an object recognition application 14. The object recognition application 14 may be downloaded from a server and stored in the memory 12 of the mobile device 10. Alternatively, the object recognition application 14 may be pre-installed and stored in a memory in the integrated circuit 46. In such an embodiment, the user may not need to download the object recognition application 14 from a server. In some embodiments, the processor 11 may also be capable of operating one or more applications, such as one or more applications functioning as an artificial intelligence ("AI") engine. The processor 11 may recognize objects that it has identified in prior uses by way of the AI engine. In this way, the processor 11 may recognize specific objects and/or classes of objects, and store information related to the recognized objects in one or more memories and/or databases discussed herein. Once the AI engine has thereby "learned" of an object and/or class of objects, the AI engine may run concurrently with and/or collaborate with other modules or applications described herein to perform the various steps of the methods discussed. For example, in some embodiments, the AI engine recognizes an object that has been recognized before and stored by the AI engine. The AI engine may then communicate to another application or module of the mobile device and/or server, an indication that the object may be the same object previously recognized. In this regard, the AI engine may provide a baseline or starting point from which to determine the nature of the object. In other embodiments, the AI engine's recognition of an object is accepted as the final recognition of the object.

The integrated circuit 46 may include the necessary circuitry to provide the object recognition functionality to the mobile device 10. Generally, the integrated circuit 46 will include data storage 48 which may include data associated with the objects within a video stream that the object recognition application 14 identifies as having a certain marker(s) (discussed in relation to FIG. 2). The integrated circuit 46 and/or data storage 48 may be an integrated circuit, a microprocessor, a system-on-a-integrated circuit, a microcontroller, or the like. As discussed above, in one embodiment, the integrated circuit 46 may provide the functionality to the mobile device 10.

Of note, while FIG. 1 illustrates the integrated circuit 46 as a separate and distinct element within the mobile device 10, it will be apparent to those skilled in the art that the object recognition functionality of integrated circuit 46 may be incorporated within other elements in the mobile device 10. For instance, the functionality of the integrated circuit 46 may be incorporated within the mobile device memory 12 and/or processor 11. In a particular embodiment, the functionality of the integrated circuit 46 is incorporated in an element within the mobile device 10 that provides object recognition capabilities to the mobile device 10. Still further, the integrated circuit 46 functionality may be included in a removable storage device such as an SD card or the like.

The processor 11 may be configured to use the network interface 34 to communicate with one or more other devices on a network. In this regard, the network interface 34 may include an antenna 42 operatively coupled to a transmitter 40 and a receiver 36 (together a "transceiver"). The processor 11 may be configured to provide signals to and receive signals from the transmitter 40 and receiver 36, respectively. The signals may include signaling information in accordance with the air interface standard of the applicable cellular system of the wireless telephone network that may be part of the network. In this regard, the mobile device 10 may be configured to operate with one or more air interface standards, communication protocols, modulation types, and access types. By way of illustration, the mobile device 10 may be configured to operate in accordance with any of a number of first, second, third, and/or fourth-generation communication protocols and/or the like. For example, the mobile device 10 may be configured to operate in accordance with second-generation (2G) wireless communication protocols IS-136 (time division multiple access (TDMA)), GSM (global system for mobile communication), and/or IS-95 (code division multiple access (CDMA)), or with third-generation (3G) wireless communication protocols, such as Universal Mobile Telecommunications System (UMTS), CDMA2000, wideband CDMA (WCDMA) and/or time division-synchronous CDMA (TD-SCDMA), with fourth-generation (4G) wireless communication protocols, and/or the like. The mobile device 10 may also be configured to operate in accordance with non-cellular communication mechanisms, such as via a wireless local area network (WLAN) or other communication/data networks.

The network interface 34 may also include an object recognition interface 38 in order to allow a user to execute some or all of the above-described processes with respect to the object recognition application 14 and/or the integrated circuit 46. The object recognition interface 38 may have access to the hardware, e.g., the transceiver, and software previously described with respect to the network interface 34. Furthermore, the object recognition interface 38 may have the ability to connect to and communicate with an external data storage on a separate system within the network as a means of recognizing the object(s) in the video stream.

As described above, the mobile device 100 may have a user interface that includes user output devices 22 and/or user input devices 28. The user output devices 22 may include a display 24 (e.g., a liquid crystal display (LCD) or the like) and a speaker 26 or other audio device, which are operatively coupled to the processor 11. The user input devices 28, which may allow the mobile device 10 to receive data from a user, may include any of a number of devices allowing the mobile device 10 to receive data from a user, such as a keypad, keyboard, touch-screen, touchpad, microphone, mouse, joystick, other pointer device, button, soft key, and/or other input device(s).

The mobile device 10 may further include a power source 32. Generally, the power source 32 is a device that supplies electrical energy to an electrical load. In one embodiment, power source 32 may convert a form of energy such as solar energy, chemical energy, mechanical energy, etc. to electrical energy. Generally, the power source 32 in a mobile device 10 may be a battery, such as a lithium battery, a nickel-metal hydride battery, or the like, that is used for powering various circuits, e.g., the transceiver circuit, and other devices that are used to operate the mobile device 10. Alternatively, the power source 32 may be a power adapter that can connect a power supply from a power outlet to the mobile device 10. In such embodiments, a power adapter may be classified as a power source "in" the mobile device.

The mobile device 10 may also include a memory 12 operatively coupled to the processor 11. As used herein, memory may include any computer readable medium configured to store data, code, or other information. The memory 12 may include volatile memory, such as volatile Random Access Memory (RAM) including a cache area for the temporary storage of data. The memory 12 may also include non-volatile memory, which can be embedded and/or may be removable. The non-volatile memory may additionally or alternatively include an electrically erasable programmable read-only memory (EEPROM), flash memory or the like.

The memory 12 may store any of a number of applications or programs which comprise computer-executable instructions/code executed by the processor 11 to implement the functions of the mobile device 10 described herein. For example, the memory 12 may include such applications as an object recognition application 14, an augmented reality (AR) presentation application 17 (described infra. in relation to FIG. 3), a web browser application 16, a Short Message Service (SMS) application 18, an electronic mail (i.e., email) application 20, etc.

Referring to FIG. 2, a block diagram illustrating an object recognition experience 60 in which a user 62 utilizes a mobile device 10 to capture a video stream that includes an environment 68 is shown. As denoted earlier, the mobile device 10 may be any mobile communication device. The mobile device 10 has the capability of capturing a video stream of the surrounding environment 68. The video capture may be by any means known in the art. In one particular embodiment, the mobile device 10 is a mobile telephone equipped with an image capture device 44 capable of video capture.

The environment 68 contains a number of objects 64. Some of such objects 64 may include a marker 66 identifiable to an object recognition application that is either executed on the mobile device 10 or within the wireless network. A marker 66 may be any type of marker that is a distinguishing feature that can be interpreted by the object recognition application to identify specific objects 64. For instance, a marker 66 may be alpha-numeric characters, symbols, logos, shapes, ratio of size of one feature to another feature, a product identifying code such as a bar code, electromagnetic radiation such as radio waves (e.g., radio frequency identification (RFID)), architectural features, color, etc. In some embodiments, the marker 66 may be audio and the mobile device 10 may be capable of utilizing audio recognition to identify words or unique sounds broadcast. The marker 66 may be any size, shape, etc. Indeed, in some embodiments, the marker 66 may be very small relative to the object 64 such as the alpha-numeric characters that identify the name or model of an object 64, whereas, in other embodiments, the marker 66 is the entire object 64 such as the unique shape, size, structure, etc.

In some embodiments, the marker 66 is not actually a physical marker located on or being broadcast by the object 64. For instance, the marker 66 may be some type of identifiable feature that is an indication that the object 64 is nearby. In some embodiments, the marker 66 for an object 64 may actually be the marker 66 for a different object 64. For example, the mobile device 10 may recognize a particular building as being "Building A." Data stored in the data storage 48 may indicate that "Building B" is located directly to the east and next to "Building A." Thus, markers 66 for an object 64 that are not located on or being broadcast by the object 64 are generally based on fixed facts about the object 64 (e.g., "Building B" is next to "Building A"). However, it is not a requirement that such a marker 66 be such a fixed fact. The marker 66 may be anything that enables the mobile device 10 and associated applications to interpret to a desired confidence level what the object is. For another example, the mobile device 10, object recognition application 14 and/or AR presentation application 17 may be used to identify a particular person as a first character from a popular show, and thereafter utilize the information that the first character is nearby features of other characters to interpret that a second character, a third character, etc. are nearby, whereas without the identification of the first character, the features of the second and third characters may not have been used to identify the second and third characters. This example may also be applied to objects outside of people.

The marker 66 may also be, or include, social network data, such as data retrieved or communicated from the Internet, such as tweets, blog posts, social networking site posts, various types of messages and/or the like. In other embodiments, the marker 66 is provided in addition to social network data as mentioned above. For example, the mobile device 10 may capture a video stream and/or one or more still shots of a large gathering of people. In this example, as above, one or more people dressed as characters in costumes may be present at a specified location. The mobile device 10, object recognition application 14, and/or the AR presentation application 17 may identify several social network indicators, such as posts, blogs, tweets, messages, and/or the like indicating the presence of one or more of the characters at the specified location. In this way, the mobile device 10 and associated applications may communicate information regarding the social media communications to the user and/or use the information regarding the social media communications in conjunction with other methods of object recognition. For example, the mobile device 10 object recognition application 14, and/or the AR presentation application 17 performing recognition of the characters at the specified location may confirm that the characters being identified are in fact the correct characters based on the retrieved social media communications. This example may also be applied objects outside of people.

In some embodiments, the mobile device and/or server access one or more other servers, social media networks, applications and/or the like in order to retrieve and/or search for information useful in performing an object recognition. In some embodiments, the mobile device and/or server accesses another application by way of an application programming interface or API. In this regard, the mobile device and/or server may quickly search and/or retrieve information from the other program without requiring additional authentication steps or other gateway steps.

While FIG. 2 illustrates that the objects 64 with markers 66 only include a single marker 66, it will be appreciated that the object 64 may have any number of markers 66 with each equally capable of identifying the object 66. Similarly, multiple markers 66 may be identified by the mobile device 10 and associated applications such that the combination of the markers 66 may be utilized to identify the object 66. For example, the mobile device 10 may utilize facial recognition markers 66 to identify a person and/or utilize a separate marker 66, such as the clothes the person is wearing to confirm the identification to the desired confidence level that the person is in fact the person the mobile device identified. For example, the facial recognition may identify a person as a famous athlete, and thereafter utilize the uniform the person is wearing to confirm that it is in fact the famous athlete.

In some embodiments, a marker 66 may be the location of the object 64. In such embodiments, the mobile device 10 may utilize Global Positioning System (GPS) hardware and/or software or some other location determining mechanism to determine the location of the user 62 and/or object 64. As noted above, a location-based marker 66 could be utilized in conjunction with other non-location-based markers 66 identifiable and recognized by the mobile device 10 to identify the object 64. However, in some embodiments, a location-based marker may be the only marker 66. For instance, in such embodiments, the mobile device 10 may utilize GPS software to determine the location of the user 62 and a compass device or software to determine what direction the mobile device 10 is facing in order to identify the object 64. In still further embodiments, the mobile device 10 does not utilize any GPS data in the identification. In such embodiments, markers 66 utilized to identify the object 64 are not location-based.

FIG. 3 illustrates a mobile device 10, specifically the display 24 of the mobile 10, wherein the device 10 has executed an object recognition application 14 and an AR presentation application 17 to present within the display 24 indications of recognized objects within the live video stream (i.e., surrounding environment 68). The mobile device 10 is configured to rely on markers 66 to identify objects 64 that are associated with product offers, products with extended warranties, new products and the like, and indicate to the user 62 the identified objects 64 by displaying an indicator 70 on the mobile device display 130 in conjunction with display of the live video stream. As illustrated, if an object 64 does not have any markers 66 (or at least enough markers 66 to yield object identification), the object 64 will be displayed without an associated indicator 70.

The object recognition application 14 may use any type of means in order to identify desired objects 64. For instance, the object recognition application 14 may utilize one or more pattern recognition algorithms to analyze objects in the environment 68 and compare with markers 66 in data storage 48 which may be contained within the mobile device 10 (such as within integrated circuit 46) or externally on a separate system accessible via the connected network. For example, the pattern recognition algorithms may include decision trees, logistic regression, Bayes classifiers, support vector machines, kernel estimation, perceptrons, clustering algorithms, regression algorithms, categorical sequence labeling algorithms, real-valued sequence labeling algorithms, parsing algorithms, general algorithms for predicting arbitrarily-structured labels such as Bayesian networks and Markov random fields, ensemble learning algorithms such as bootstrap aggregating, boosting, ensemble averaging, combinations thereof, and the like.

Upon identifying an object 64 within the real-time video stream, the AR presentation application 17 is configured to superimpose an indicator 70 on the mobile device display 24. The indicator 70 is generally a graphical representation that highlights or outlines the object 64 and may be activatable (i.e., include an embedded link), such that the user 62 may "select" the indicator 70 and retrieve information related to the identified object. The information may include any desired information associated with the selected object and may range from basic information to greatly detailed information. In some embodiments, the indicator 70 may provide the user 62 with an internet hyperlink to further information on the object 64. The information may include, for example, all types of media, such as text, images, clipart, video clips, movies, or any other type of information desired. In yet other embodiments, the indicator 70 information related to the identified object may be visualized by the user 62 without "selecting" the indicator 70.

In embodiments in which the indicator 70 provides an interactive tab to the user 62, the user 62 may select the indicator 70 by any conventional means, e.g., keystroke, touch, voice command or the like, for interaction with the mobile device 10. For instance, in some embodiments, the user 62 may utilize an input device 28 such as a keyboard to highlight and select the indicator 70 in order to retrieve the information. In a particular embodiment, the mobile device display 24 includes a touch screen that the user may employ to select the indicator 70 utilizing the user's finger, a stylus, or the like.

In some embodiments, the indicator 70 is not be interactive and simply provides information to the user 62 by superimposing the indicator 70 onto the display 24. For example, in some instances it may be beneficial for the AR presentation application 17 to merely identify an object 64, e.g., just identify the object's name/title, give brief information about the object, etc., rather than provide extensive detail that requires interaction with the indicator 70. The AR presentation application 17 is capable of being tailored to a user's desired preferences.

Furthermore, the indicator 70 may be displayed at any size on the mobile device display 24. The indicator 70 may be small enough that it is positioned on or next to the object 64 being identified such that the object 64 remains discernable behind the indicator 70. Additionally, the indicator 70 may be semi-transparent or an outline of the object 64, such that the object 64 remains discernable behind or enclosed by the indicator 70. In other embodiments, the indicator 70 may be large enough to completely cover the object 64 portrayed on the display 24. Indeed, in some embodiments, the indicator 70 may cover a majority or the entirety of the mobile device display 24.

The user 62 may opt to execute the object recognition application 14 and AR presentation application 17 at any desired moment and begin video capture and analysis. However, in some embodiments, the object recognition application 14 and AR presentation application 17 includes an "always on" feature in which the mobile device 10 is continuously capturing video and analyzing the objects 64 within the video stream. In such embodiments, the object recognition application 14 may be configured to alert the user 62 that a particular object 64 has been identified. The user 62 may set any number of user preferences to tailor the object recognition and AR presentation experience to their needs. For instance, the user 62 may opt to only be alerted if a certain particular object 64 is identified. Additionally, it will be appreciated that the "always on" feature in which video is continuously captured may consume the mobile device power source 32 more quickly. Thus, in some embodiments, the "always on" feature may disengage if a determined event occurs such as low power source 32, low levels of light for an extended period of time (e.g., such as if the mobile device 10 is in a user's pocket obstructing a clear view of the environment 68 from the mobile device 10), if the mobile device 10 remains stationary (thus receiving the same video stream) for an extended period of time, the user sets a certain time of day to disengage, etc. Conversely, if the "always on" feature is disengaged due to the occurrence of such an event, the user 62 may opt for the "always on" feature to re-engage after the duration of the disengaging event (e.g., power source 32 is re-charged, light levels are increased, etc.).

In some embodiments, the user 62 may identify objects 64 that the object recognition application 14 does not identify and add it to the data storage 48 with desired information in order to be identified and/or displayed in the future. For instance, the user 62 may select an unidentified object 64 and enter a name/title and/or any other desired information for the unidentified object 64. In such embodiments, the object recognition application 14 may detect/record certain markers 66 about the object so that the pattern recognition algorithm(s) (or other identification means) may detect the object 64 in the future. Furthermore, in cases where the object information is within the data storage 48, but the object recognition application 14 fails to identify the object 64 (e.g., one or more identifying characteristics or markers 66 of the object has changed since it was added to the data storage 48 or the marker 66 simply was not identified), the user 62 may select the object 64 and associate it with an object 64 already stored in the data storage 48. In such cases, the object recognition application 14 may be capable of updating the markers 66 for the object 64 in order to identify the object in future video streams.

In addition, in some embodiments, the user 62 may opt to edit the information or add to the information provided by the indicator 70. For instance, the user 62 may opt to include user-specific information about a certain object 64 such that the information may be displayed upon a future identification of the object 64. Conversely, in some embodiments, the user may opt to delete or hide an object 64 from being identified and an indicator 70 associated therewith being displayed on the mobile device display 24.

Furthermore, in some instances, an object 64 may include one or more markers 66 identified by the object recognition application 14 that leads the object recognition application 14 to associate an object with more than one objects in the data storage 48. In such instances, the user 62 may be presented with multiple candidate identifications and may opt to choose the appropriate identification or input a different identification. The multiple candidates may be presented to the user 62 by any means. For instance, in one embodiment, the candidates are presented to the user 62 as a list wherein the "strongest" candidate is listed first based on reliability of the identification. Upon input by the user 62 identifying the object 64, the object recognition application 14 may "learn" from the input and store additional markers 66 in order to avoid multiple identification candidates for the same object 64 in future identifications.

Additionally, the object recognition application 14 may utilize other metrics for identification than identification algorithms. For instance, the object recognition application 14 may utilize the user's location, time of day, season, weather, speed of location changes (e.g., walking versus traveling), "busyness" (e.g., how many objects are in motion versus stationary in the video stream), as well any number of other conceivable factors in determining the identification of objects 64. Moreover, the user 62 may input preferences or other metrics for which the object recognition application 14 may utilize to narrow results of identified objects 64.

In some embodiments, the AR presentation application 17 may have the ability to gather and report user interactions with displayed indicators 70. The data elements gathered and reported may include, but are not limited to, number of offer impressions; time spent "viewing" an offer, product, object or business; number of offers investigated via a selection; number of offers loaded to an electronic wallet and the like. Such user interactions may be reported to any type of entity desired. In one particular embodiment, the user interactions may be reported to a financial institution and the information reported may include customer financial behavior, purchase power/transaction history, and the like.

In various embodiments, information associated with or related to one or more objects that is retrieved for presentation to a user via the mobile device may be permanently or semi-permanently associated with the object. In other words, the object may be "tagged" with the information. In some embodiments, a location pointer is associated with an object after information is retrieved regarding the object. In this regard, subsequent mobile devices capturing the object for recognition may retrieve the associated information, tags and/or pointers in order to more quickly retrieve information regarding the object. In some embodiments, the mobile device provides the user an opportunity to post messages, links to information or the like and associate such postings with the object. Subsequent users may then be presenting such postings when their mobile devices capture and recognize an object. In some embodiments, the information gathered through the recognition and information retrieval process may be posted by the user in association with the object. Such tags and/or postings may be stored in a predetermined memory and/or database for ease of searching and retrieval.

Referring to FIG. 4, an apparatus 100 configured for presenting medical condition related information (MCRI) in a live video stream, in accordance with embodiments of the present invention. The apparatus includes a computing platform 102 having a processor 104 and a memory 106 in communication with the processor. Additionally, apparatus 100 includes image capture device 108 and display 110 both in communication with processor 104.

It should be noted that the apparatus 100 may include more than one computing device. For example, apparatus 100 may include a mobile communication device and a network device, which operate in unison to present MCRI in a live video stream displayed on a display of the mobile communication device. Thus, the logic shown and described in apparatus 100 may reside and be executed on a mobile communication device or a network device that is in wireless communication with the mobile communication device. A mobile communication device may be a mobile cellular telephone, such as a smart phone or the like, a Personal Data Assistant (PDA) a tablet computing device, a laptop device or any other computing device having an image capture device 108 and a display 110. It should be noted that while many embodiments of the mobile communication device are personal and/or handheld devices, in other embodiments of the invention a mobile communication device may be permanently or temporarily located within a moving vehicle, such as an automobile or the like.

The memory 106 of apparatus 100 includes image capture logic 112 that is in communication with image capture device 108 and configured to capture a video stream 114. It should be noted that the video stream 114 may be captured from various different environments. For example, the video stream 114 may be captured as a user directs the image capture device 108 to focus on the user's body where the user has a medical condition such as an injury, wound, rash, or other visible condition. The medical condition may also be an internal condition that may be recognized by ultrasound or other noninvasive vision method. As another example, the video stream 114 may be captured in conjunction with one or more other inputs such as audio input. For example, an audio input may be provided that recognizes heartbeat of the patient based on sound waves. As another example, a user may swallow a sensor configured to communicate information to the user's mobile device. In some embodiments, the information communicated relates to gastro-intestinal conditions or other internal conditions of the user. In some embodiments, the internal information is combined with external information provided based on images captured from the video stream.

The video stream 114 may also be captured as a user directs the image capture device 108 to focus on one or more products, such as while shopping in a retail location, such as an aisle of a grocery store, department store, home improvement store, physician's office, pharmacy or the like. In addition, the video stream 114 may be captured in the user residence, such as video of the contents of a medicine cabinet, pantry, cupboard, storage area, a refrigerator or the like. In other embodiments, the video stream 114 may be captured while watching media, such as television, Internet or the like, reading media, such as via the Internet, a billboard advertisement, magazine, newspaper or the like.

In some embodiments, the information provided by the real-time video stream may be compared to data provided to the system through an API. In this way, the data may be stored in a separate API and be implemented by request from the mobile device and/or server.

The memory 106 of apparatus 100 additionally includes medical condition identification logic 118 that is configured to identify one or more medical conditions 116 in the video stream 114. For purposes of this disclosure medical conditions 116 may be or include one or more of external bodily conditions, internal bodily conditions, topical bodily conditions, injuries, wounds, rashes and the like. In some embodiments, the memory 106 of apparatus 100 also includes product identification logic (not shown) that is configured to identify one or more products in the video stream 114. For purposes of this disclosure products may include products, services and entities associated with products or services, such as business entities, manufacturers or the like. The medical condition identification logic 118 may implement any known or future known identification mechanisms. For example, medical condition identification logic may implement image recognition techniques based on characteristics, shapes, shades or colors, sizes, and the like associated with a medical condition. Similarly, product identification logic may implement image recognition techniques based on characteristics, indicia (e.g., Optical Character Recognition (OCR) or the like), logos, shapes and the like associated with a product. In addition, in those embodiments in which the products or tags displayed in conjunction with the products include a visually readable code, such as Quick Response (QR) code, bar code or the like, the product identification logic may be implemented to decipher the code to identify the product.

In other embodiments of the invention, the medical condition identification logic 118 may identify the one or more medical conditions 116 based on the geographic location of the user or information communicated from the user, such as that the user has been swimming in the ocean. In such a case, the likelihood of a medical condition such as a jellyfish sting is much more likely. Since medical condition identification based on location information and/or information communicated from the medical conditions may not necessarily rely on an image for identification, such identification may be lieu of or implemented in combination with visual identification techniques described above.

In other embodiments of the invention, the product identification logic may identify the one or more products based on the geographic location of the products or information communicated from the products. In such embodiments, the product identification logic may be configured to identify products by implementing geo-fencing techniques or any other spatial technique. In other such embodiments, the product identification logic may be configured to sense and receive short range communication, such as via Near Field Communication (NFC), Radio Frequency Identification (RFID), Bluetooth® or the like, which includes identification of the products. Since product identification based on location and/or information communicated from the products does not rely on an image for identification, such identification may be lieu of or implemented in combination with visual identification techniques described above.

The memory 106 of apparatus 100 additionally includes medical condition information (MCRI) determination logic 120 configured to determine if an identified medical condition 116 currently has associated medical condition information. The medical condition information may include, in various embodiments, information corresponding to the user of the apparatus, such as a user of a mobile device, or in various other embodiments, the medical condition information may include information related to the medical condition itself, such as information regarding the proper treatment of the medical condition. In some embodiments, the MCRI includes information related to the specific user and/or the medical condition and/or any product(s) that may be used in treatment of the medical condition. Such information may include, for example, information related to alternative salves for use in treating an identified skin condition or may include information related to a recommended timeline and treatment regimen for a medical condition, including information regarding the proposed product(s).

The MCRI, in various embodiments, where the object is a drug or medicine or is related to a drug or medicine, may include a cross reference to the user's current medicines and may include information regarding how the user's current medicines may affect the treatment regimen for the identified medical condition. The MCRI may include information regarding the user's propensities for sustaining specific injuries, such as historical information regarding the user's prior injuries or information regarding the potential cross reactivity among medicines the user is already taking and/or any medicines proposed for treatment of an identified medical condition. The MCRI may include information regarding generic drugs versus brand drugs determined to be potentially beneficial for use in treatment of an identified medical condition and/or comparisons between the drugs, such as, information and/or comparisons regarding ingredients, price, user reviews, and the like. The MCRI may include information and/or pointers to information regarding medical records related to a physician recommendation and/or prescription associated with a recommended treatment regimen for the medical condition. In various embodiments, the information may be related to the user's medical records and/or the medical records of someone else, such as the user's family member, friend or child. The MCRI may include information related to any adverse effects the user experienced when taking certain medicine(s) in the past. The user, in some embodiments, inputs such information and it is stored, and in other embodiments, such information is retrieved from medical records. Finally, in some embodiments, the MCRI may include information or pointers to information posted or published by a third party, such as an expert physician in the applicable field.

In various embodiments, the MCRI includes information or pointers to information regarding video instructions and/or video prescriptions recorded by the user's physician or some other physician and related to the medical condition, such as information regarding treatment of an identified medical condition. For example, in some embodiments, the information may include first aid instructions for treating a broken limb, a cut, a bruise, a scrape, a twisted ankle, or the like. Further, such information may be based on the identified severity of the medical condition based on recognition by the mobile device, based on predetermined severity, such as a high severity for any broken limb, and/or based on explicit user input to the mobile device.

In some embodiments, the MCRI includes information regarding the likelihood of a user in general or the specific user to adherence to taking a particular medication. Such information may be useful to the user in determining which of a set of proposed treatment regimens to choose. That is, the user may desire to choose a less comprehensive treatment regimen to ensure that the user will, in fact, complete the treatment regimen despite the treatment regimen possibly being less effective than a more strenuous proposed treatment regimen. In some such embodiments, upon receiving input from the user regarding a choice for a treatment regimen that was recommended by the system, the system provides one or more rewards. In this regard, in some cases, the user is presented with one or more incentives for choosing the treatment regimen, which of course, may be more rigorous, recommended by the system. Thus, the system may influence the user to choose a more effective treatment regimen.

In some embodiments, the MCRI includes information regarding other retailers in the vicinity of the user currently making offers on one or more of the products associated with treatment of the medical condition. In some embodiments, the MCRI includes information regarding retailers issuing coupons or rewards, and/or the like, thereby potentially making one or more products more attractive at the user's current location or other, competing location. Similarly, the MCRI may provide information regarding the lowest price, which is, in some embodiments, filtered only for brick and mortar retailers or online retailers. In some embodiments, the mobile device provides the user an opportunity to purchase from the current retailer or another retailer. In some embodiments, once the user has chosen a product associated with treatment of the medical condition for purchase, the device automatically purchases the product, such as through an online transaction, from the current retailer or another retailer, either brick and mortar or online. In some embodiments, the MCRI includes one or more recommendations regarding physician, such as a specialist, or other medical professional for treating and/or providing information regarding the medical condition. In some embodiments, the system, upon approval from the user, or in some embodiments, automatically, schedules an appointment for the user with the recommended medical professional. In some embodiments, the user is connected automatically with the medical professional's office via telephone or other communication pathway for interaction, such as for scheduling an appointment.

The MCRI may include purchase history, either of a particular product or corresponding to the user's purchases. The MCRI may include information regarding whether the product was used for any other medical conditions in the past. In some embodiments, the MCRI includes information regarding whether any friends or members of a social network posted any information regarding the product and/or whether they posted any information regarding the medical condition in general and/or related to person treatment regimens for the medical condition. In some embodiments, the MCRI may include an avatar-based intelligent agent configured to evaluate the medical condition, such as, an avatar illustrated to look like a health care professional such as a doctor, for health information and provide a recommendation for treatment such as proposed product usage.

MCRI determination logic 120 is in communication with MCRI database 124 which stores MCRI 122 for medical conditions 116 and/or products. The MCRI determination logic 120 may be configured by the user or by the entity providing for the MCRI program. For example, the user may configure the apparatus 100 such that only MCRI 122 of a certain type is determined, such as MCRI for a specific medical condition and/or product, a specific set of medical conditions, such as skin conditions, blood conditions, heart conditions, respiratory conditions, and the like, or brand of product, a specific provider/retailer of the product or the like. In additional embodiments, the entity providing the MCRI program may configure the apparatus 100 such that only MCRI 122 from, with regard to medical conditions, predetermined health care providers, such as the user's personal doctor, pharmacist or the like, or from, with regard to products, predetermined manufacturers, retailers, medicinal suppliers, physicians and the like are determined. For example, only manufacturers and/or retailers that are affiliated or otherwise have a relationship with the entity providing the MCRI program may be presented.

The memory 106 of apparatus 100 additionally includes MCRI presentation logic 126 that is configured to present one or more MCRI indicators 128, on a display of mobile communication device, each MCRI indicator 128 presented in a live video stream 130 proximate a location of the one or more medical conditions 116 or products 116 determined to be associated with MCRI 122.

In some embodiments, the MCRI presentation logic 126 is configured for presenting the MCRI by itself. That is, the MCRI is presented in response to the user's selection of an indicator associated with an object, such as a medical condition or product, and is presented instead of the real-time video stream. In some embodiments, the MCRI presentation logic 126 is configured to present a website related to the MCRI, such as a website detailing the user's health information and the potential or predetermined perceived impact of the product on the user's specific medical condition. Similarly, a website may be presented that is related to the diagnosis and characteristics of the medical condition. In various embodiments, for example, the MCRI presentation logic 126 is configured to access information related to the identified medical condition, such as the medical condition's appearance, symptoms, duration, diagnosis, treatment and the like. The MCRI presentation logic is also configured to determine the ingredients in a product such as a medicine and thereafter present information regarding the perceived impact of the product on the user should the user ingest or otherwise use the product or medicine for treatment of the medical condition. The MCRI presentation logic, in some embodiments, may correlate the user's medical history or other information regarding the user's health with the product proposed for treatment of the identified medical condition, and thereby, may present information specific to the user regarding use of the product to treat the medical condition. For example, based on the user's medical history, the proposed medicine may not be recommended because of a potential allergic reaction, and therefore, an alternative may be proposed. In some embodiments, the MCRI presentation logic is configured to access known medication treatment plans and present information regarding the treatment plan to the user and/or present information regarding the perceived impact of using a medicine based on a known medication treatment plan. In some embodiments, the MCRI presentation logic 126 is further configured for presenting one or more indicators indicating to a user whether to consider a particular product or medicine given the user's specific health situation. The MCRI presentation logic, in some embodiments, is further configured to present to the user an indicator, such as a large red "X" overlaid on the real-time video stream representation of the product. Thus, the user is made aware of the danger of that particular product or medicine based on the user's specific health situation. Alternatively, of course, the MCRI presentation logic is configured to present to the user an indicator highlighting those product(s) which may be of particular use in treatment of the identified medical condition.

In various embodiments of the invention the MCRI indicator 128 may be a graphical tag, highlighted area or an outline around the border of the medical condition 116 and/or product as displayed in the live video stream 130. As discussed in the example above, a user of the mobile communication device may activate the MCRI indicator 128, through touch, mouse-pointer click, keypad, voice command or the like, to display further information regarding the MCRI 122 (e.g., additional resources for information, potential health implications or affects on a user's predetermined health goals, such as losing weight, and the like), download the MCRI associated with a medical condition to their mobile communication device for subsequent consideration during a product purchasing decision or, for example, during administration of a medicinal product and/or initiate network communication with a website or the like for retrieving additional information on the medical condition and/or product and conducting a transaction to purchase the product associated with treatment of the identified medical condition.

In specific embodiments of the invention, the user of the mobile communication device may be actively "looking" for MCRI by positioning the image capture device 108 in front of medical conditions 116 and/or products so as to capture the video stream 114, subsequently identify the medical conditions 116 and/or products, determine if any MCRI is associated with the medical conditions 116 and/or products and present the MCRI indicators 128 in the live video stream 130 that the user is viewing. For example, the user positions the mobile device to scan a body part, such as the user's shin or the aisle of a pharmacy, grocery store or their pantry within their residence. In some embodiments, the mobile device may be configured to recommend combining medical conditions to determine a diagnosis and/or to recommend combining products to create a complete treatment regimen associated with a specific diagnosis and/or medical condition(s). For example, the mobile device may put together products form a cabinet, grocery stores or other area. As the user moves through the location, the device may identify the predetermined products that should be part of the treatment regimen. In this regard, the device provides the user a treatment regimen dynamically created over time.

In other specific embodiments of the invention, the user may be passively "looking" for MCRI associated with one or more medical conditions and/or products, such as when the apparatus 100 has been configured to search for user-specified MCRI or the like. In such a passive mode, the mobile communication device may be in a continuously-on mode and/or automatically turned on and off on a predetermined periodical schedule (i.e., intermittent mode). In the passive mode, determination and presentation of an MCRI may require that the user be prompted to notify the user of the MCRI associated with a medical condition and/or product. The prompt may include communicating an alert to the user, such as an audio alert communicated from the mobile communication device, e.g., an audible alarm or the like, and/or a visual alert, e.g., display of a flashing light on the mobile communication device or the like. For example, while the user is sunbathing on vacation, the user's mobile device recognizes that the user is getting sunburned. The mobile device provides an alert to the user that the sunburn is worsening, and in some embodiments, provides potential treatment options, such as products available for purchase at a nearby retailer. In some embodiments, such a product may be purchased using the mobile device over the Internet and the user may then retrieve the purchased item at the nearby retailer for use in treating the medical condition. In some embodiments, the mobile device includes an ultraviolet sensor configured for sensing an amount of radiation received, such as from the sun while outdoors. Information regarding radiation received may be presented to the user as MCRI.

In some embodiments of the invention, the mobile device and/or server may also include medical condition communication logic (not shown) configured to communication information regarding the medical condition to one or more medical professionals. For example, in some embodiments, the logic communicates medical condition identification and/or determination information to the user's personal care physician or other predetermined individual or individuals. In other embodiments, where the medical condition is serious and/or life threatening, 911 emergency services and/or others emergency entities are contacted and information regarding the medical may be relayed. In some embodiments, information regarding the medical condition may be communicated to first responders such as police, ambulance personnel and/or firefighters responding to a call regarding the user and the medical condition. Some of the information that may be communicated includes streaming video of the medical condition, video regarding the treatment of the medical condition, pictures of the medical condition and/or treatment of the medical condition, statistics and/or additional information sensed from other sensors disposed with the mobile device.

In some embodiments, the medical condition communication logic is configured for providing information directly to a medical professional's mobile device or other computing device in the event the user has a medical condition requiring attention. In some embodiments, the user may request communication of information regarding the medical condition to the user's physician, for example. The information that may be communicated to the medical professional may include streaming video regarding the medical condition.

FIG. 5 is an additional block diagram regarding presenting MCRI in conjunction with a live video stream, in accordance with embodiments of the present invention. In addition to highlighting and describing further details of the invention, FIG. 5 provides for alternate embodiments of the invention. The apparatus 400 includes a computing platform 102 having at least one processor 104 and a memory 106 in communication with the processor. The apparatus, in various embodiments, may be a server of bank of servers or other computing devices remote from a mobile communication device and in communication with a mobile communication device over a network. Memory 106 may be resident on the apparatus 400 or at least a portion of memory 106 may be remote memory that is network accessible to the server and/or the mobile communication device, for example, at least a portion of memory 106 may reside on servers or the like as part of the offer providing entity's network. Memory 106 may comprise volatile and nonvolatile memory such as read-only and/or random-access memory (RAM and ROM), EPROM, EEPROM, flash cards, or any memory common to computing platforms. Further, memory 106 may include one or more flash memory cells, or may be any secondary or tertiary storage device, such as magnetic media, optical media, tape, or soft or hard disk.

Processor 104 may be an application-specific integrated circuit ("ASIC"), or other integrated circuit set, processor, logic circuit, or other data processing device. Processor 104 or other processor such as an Application Specific Integrated Circuit (ASIC) may execute an application programming interface ("API") layer (not shown in FIG. 5) that interfaces with any resident programs or modules, such as medical condition identification logic 118, product identification logic, MCRI determination logic 120, and MCRI presentation logic 130 stored in the memory 106 of the apparatus 100 and/or apparatus 400.

Processor 104 may include various processing subsystems (not shown in FIG. 5) embodied in hardware, firmware, software, and combinations thereof, that enable the functionality of apparatus 100 and/or apparatus 400 and the operability of the apparatus 100 and/or apparatus 400 on a network. For example, processing subsystems allow for initiating and maintaining communications, and exchanging data, with other networked devices. For the disclosed embodiments, processing subsystems of apparatus 100 and/or apparatus 400 may include any subsystem used in conjunction with applications, modules, components and routines described herein.

As previously discussed, the memory 106 of apparatus 100 includes image capture logic 112 that is in communication with image capture device 108 and configured to capture a video stream 114. Additionally, memory 106 includes medical condition identification logic 118 that is configured to identify one or more medical conditions 116 in the video stream 114. For purposes of this disclosure medical conditions 116 may be or include one or more of external bodily conditions, internal bodily conditions, topical bodily conditions, injuries, wounds, rashes and the like. Memory 106 may also include product identification logic (not shown) that may implement image recognition techniques based on characteristics, indicia (e.g., Optical Character Recognition (OCR) or the like), logos, shapes and the like associated with a product. In addition, in those embodiments in which the products or tags displayed in conjunction with the products include a visually readable code, such as Quick Response (QR) code, bar code or the like, the product identification logic 118 may be implemented to decipher the code to identify the product.

The memory 106 of apparatus 100 additionally includes MCRI determination logic 120 configured to determine if an identified medical condition 116 and/or product 404 has associated MCRI 122. Thus, MCRI determination logic 120 is in communication with database 403 which stores MCRI 122, 408 and 410 for medical conditions 116 and products 404 and 406. Products 404 and 406 are associated, respectively, with MCRI 408 and MCRI 410. In various embodiments, the products 404 and 406 are products that are presented as potential or recommended treatment options or as inclusions in a recommended treatment regimen for a previously identified medical condition or conditions. In other embodiments, product 404 and product 406 represent alternatives to one another and MCRI 408 and 410 may include information to assist the user in choosing which alternative to purchase.

Additionally, in specific embodiments of the invention, memory 106 of apparatus 400 includes communication logic 402 that is configured to create and communicate instructions from apparatus 400 (e.g, server) to apparatus 100 (e.g., mobile communication device) in order to initiate display of a presentation of the MCRI in conjunction with the real-time video stream or other type of display, such as merely displaying the MCRI. Thus, communication logic 402 is in communication with database 403, which stores MCRI 122, MCRI 408 and/or MCRI 410 for designated medical condition 116, product 404 and/or product 406, respectively.

As previously discussed in relation to FIG. 4, the memory 106 of apparatus 100 additionally includes MCRI presentation logic 126 that is configured to present one or more MCRI indicators 128 on a display of mobile communication device. Each MCRI indicator 128 is presented in a live video stream 130 proximate a location of the one or more medical conditions 116 and/or one or more products 404 and/or 406 determined to be associated with the medical condition 116 and/or associated with a product 404 and/or 406 that has been determined to be suitable for treatment of a previously identified medical condition.

In one embodiment of the invention, the MCRI indicators 128 and/or any other indicators which indicate a feature related to the MCRI associated with the medical condition and/or product may be displayed separately. In such embodiments, the user of the mobile communication device may switch between modes to display the information which they are interested in. For example, a first mode may provide for display of MCRI indicators 128, a second mode may provide for display of MCRI indicators corresponding to a different medical condition, such as a related medical condition, and/or a type of product or class of product, and a third mode may provide for display of other designated medical condition-related and/or product-related indicators and so on. Switching between modes may be configured to occur by any configurable means, such as key activation, touch screen activation, voice command or the like.

In other related embodiments of the invention, two or more MCRI indicators and/or any other indicators may be displayed in unison, such that indicators are graphically distinct, such as different colors, highlights, etc and may be configured to overlay one another. As previously noted, in one embodiment of the invention the MCRI indicators may be a graphical tag, highlighted area, such as specific color or pattern highlighting, or an outline around the border of the medical condition 116 and/or product 404 or 406 as displayed in the live video stream 130. The user of the mobile communication device may activate the indicators through touch, mouse-pointer click, keypad, voice command or the like, to display further information regarding the MCRI 122.

In one specific embodiment of the invention, the MCRI indicator 128 may be configured as a dotted-line surrounding the border of the associated product 116. The user may activate the MCRI indicator 128, such as by touching the display in the area of the product, providing the requisite key stroke or voice command or the like. Upon activation, the MCRI 122 is automatically downloaded to an MCRI database, which is sometimes referred to as electronic MCRI.

In other embodiments of the invention, other indicators, such as a solid line surrounding the border of an associated medical condition 116 and/or product 404 or 406 may be implemented to indicate that the MCRI already exists in the user's electronic MCRI. In still further embodiments of the invention, other indicators may be implemented to communicate other information about the MCRI. For example, other indicators may indicate that MCRI is out of date and the user should seek out updated MCRI from another source. In some embodiments, information regarding additional sources is presented to the user, such as, for example, information regarding one or more websites hosting additional information, such as live video chat with a life management coach, physician, nurse, peer, buddy, social network member or the like for information, consulting and/or positive feedback, and/or contact information regarding one or more people, such as physicians, nurses, pharmacists, nutritionists and the like who are trained professionals capable of providing additional and/or updated MCRI. In some embodiments, the contact information corresponds to those people within a predetermined physical radius of the user and in other embodiments the people are already associated with the user, such as in a physician-patient relationship or social network. In one specific embodiment of the invention, a blinking MCRI indicator 128 may indicate that the MCRI has some characteristic particularly useful to the user, such as the product is both assists the user to treat a previously identified medical condition as well as being low in sugar.

In other embodiments, of the invention activation of the MCRI indicator 128 may provide for the mobile communication device to initiate communication with a network entity, such as a web site or the like, configured for purchasing the product 404 or 406, or providing additional information related to the product 404 or 406.

Referring to FIG. 6 a flow diagram illustrates a method 600 for providing medical condition related information.

At Event 610, images in a video stream captured on a mobile communication device are identified as corresponding to medical condition(s) of a user. Capturing of the video stream may include, for example, positioning the mobile communication device to view, and capture the video stream of, any medical condition(s) on the user's body.

Identifying which images from the video stream are associated with medical condition(s) may include analyzing the real-time video stream for characteristics such as color, breadth, depth, size, shape and the like of the medical condition, characteristics that sometimes referred to herein as markers, to identify the images as medical condition(s).

At Event 620, one or more of the identified medical conditions are determined to currently be associated with MCRI. The MCRI may include, but is not limited to information corresponding to the user of the apparatus, such as a user of a mobile device, or in various other embodiments, the medical condition information may include information related to the medical condition itself, such as information regarding the proper treatment of the medical condition. In some embodiments, the MCRI includes information related to the specific user and/or the medical condition and/or any product(s) that may be used in treatment of the medical condition. Determination of which medical condition(s) have associated MCRI may be implemented by comparing the identified medical conditions to database listing of medical conditions currently associated with MCRI. It should be noted that in certain embodiments, user configuration may dictate which types of MCRI the user desires and, thus, which databases are accessed for searching/retrieving the MCRI or which filters are implemented within the databases for determining associated MCRI.

At Event 630, one or more indicators are presented on the display of the mobile communication device in conjunction with a live video stream. Each of the indicators is presented proximate to a location of a corresponding medical condition determined to currently have associated MCRI. As previously noted, the indicator may take various forms, such as display of a tag, a highlighted area, a hot-spot or the like. In specific embodiments, the indicator is a selectable indicator, such that a user may select (e.g., click-on, hover-over, touch the display, provide a voice command or the like) the indicator to provide display of specifics related to the MCRI, downloading the MCRI to an electronic folder, called an electronic MCRI or accessing a network entity, such as a web site, for additional information regarding the medical condition as well as potential treatment information. In other embodiments, the indicator itself may provide the MCRI or a portion of the MCRI.

In other specific embodiments, the indicator may indicate the availability of current MCRI, such as a specific color-code, shading or outlining of the product (e.g., dotted-line outlining the product). The user of the mobile communication device may select (e.g., click-on, hover-over, touch the display, provide a voice command or the like) the indicator to add some or all the MCRI to an electronic storage area, referred to herein as an electronic MCRI. MCRI that has previously been added to the electronic MCRI but has yet to have been reviewed by the user may provide for a different visual indicator than MCRI that have yet to be added to the electronic MCRI. For example, MCRI that has previously been added may be shaded differently than MCRI previously added to the electronic MCRI or may have a solid-line outlining the medical condition. Other visual indicators may indicate other features of the MCRI.

Referring to FIG. 7 a flow diagram is depicted of another method 700 for providing medical condition related information.

At Event 710, a server in communication with a mobile communication device identifies any images in a video stream captured on a mobile communication device corresponding to a medical condition. At Event 720, the server determines which of one or more medical conditions identified in the video stream have associated MCRI. At Event 730, the server communicates instructions to the mobile communication device for presenting a display of the live video stream on the mobile communication device in conjunction with one or more MCRI indicators. In some embodiments, each MCRI indicator is presented proximate a location of the one or more medical conditions determined to have associated MCRI.

Referring to FIG. 8 a flow diagram is depicted of a method 800 for providing medical condition related information in conjunction with a presentation of a product determined to be associated with treatment of a previously identified medical condition.

At Event 810, images in a video stream captured on a mobile communication device are identified as corresponding to products associated with a previously identified medical condition of the user. Capturing of the video stream may include, for example, a user moving about an aisle within a pharmacy, grocery store or other retailer while positioning the mobile communication device to view, and capture the video stream of, the products on the shelves in the aisle. In another embodiment of the invention, a user may capture a video stream within their residence, such as positioning the mobile communication device to view, and capture the video stream of, products within their cupboard/pantry or their refrigerator/freezer or the like, specific products/appliances within the residence which may need replacement or duplication, or products shown in a television commercial, online video, online advertisement, Youtube video or the like.

Identifying which images from the video stream are associated with products (including services) may include analyzing the real-time video stream for objects, logos, artwork or other product-indicating features, referred to herein as markers, to identify the images as products. As previously noted, the images may also be identified as products based on coded information, such as QR code, bar code or the like, affixed to proximate to the product. In addition, product identification may utilize Optical Character recognition (OCR), geo-fencing/position location, short range communication (e.g., NFC, RFID or the like) in addition to, or in lieu of, identification of the products based on the images captured on the mobile communication device.

At Event 820, one or more of the identified products are determined to currently be associated with MCRI. The MCRI may include, but is not limited to, nutrition information, caloric information, medical indication information, proper medicinal treatment information, financial impact information, or the like. Determination of which products have associated MCRI may be implemented by comparing the identified products to database listing of products currently associated with MCRI. The stored listing of product MCRI may be specific to the retail location at which the real-time video stream is being captured or, in other embodiments, the listing or listings of product MCRI may be specific to retail/merchant locations (physical or online) at which the user of the mobile communication typically shops or from competing retailers/merchants at which the user does not typically shop or a combination of both. In other embodiments, the listing or listings of product MCRI may be associated with one or more third-party product programs, such as a financial institution MCRI program or the like. Thus, in those embodiments in which the MCRI is not tied to the location of the real-time video stream, such as residential video stream or the like, the MCRI may be irrespective of which retailer/merchant the user typically uses and/or prefers. It should be noted that in certain embodiments, user configuration may dictate which types of MCRI the user desires and, thus, which databases are accessed for searching/retrieving the MCRI or which filters are implemented within the databases for determining associated MCRI.

At Event 830, one or more indicators are presented on the display of the mobile communication device in conjunction with a live video stream. Each of the indicators is presented proximate to a location of a corresponding product determined to currently have associated MCRI. As previously noted, the indicator may take various forms, such as display of a tag, a highlighted area, a hot-spot or the like. In specific embodiments, the indicator is a selectable indicator, such that a user may select (e.g., click-on, hover-over, touch the display, provide a voice command or the like) the indicator to provide display of specifics related to the MCRI, downloading the MCRI to an electronic folder, called an electronic MCRI or accessing a network entity, such as a web site, for purchasing the product. In other embodiments, the indicator itself may provide the MCRI or a portion of the MCRI.

In other specific embodiments, the indicator may indicate the availability of current MCRI, such as a specific color-code, shading or outlining of the product (e.g., dotted-line outlining the product). The user of the mobile communication device may select (e.g., click-on, hover-over, touch the display, provide a voice command or the like) the indicator to add some or all the MCRI to an electronic storage area, referred to herein as an electronic MCRI. MCRI that has previously been added to the electronic MCRI but has yet to have been reviewed by the user may provide for a different visual indicator than MCRI that have yet to be added to the electronic MCRI. For example, MCRI that has previously been added may be shaded differently than MCRI previously added to the electronic MCRI or may have a solid-line outlining the product. Other visual indicators may indicate other features of the MCRI, such as expirations date of the product, whether the product fits within the user's predetermined health goals, whether the product affects any of the user's predetermined allergies, or the like.

In some embodiments, the user's social network, family or friends' medical or health need are addressed by the invention. For example, the user's immediate family provides health information that is stored on one or more memories and/or databases discussed above. The health information is then used in conjunction with the real-time image analysis to determine whether and objects or products in captured in the video stream meet the wants and/or needs of one or more of the family members. For example, in some embodiments, the family members upload information regarding their health conditions, such as seasonal allergies. The father of the family, for example, while he is shopping at a grocery store is using his mobile device to identify products needed by the family. The mobile device captures images of various seasonal allergy medications and provides one or more indicators indicating which, if any, of the seasonal allergy medications to purchase. Further, in conjunction with various embodiments of the invention, various other information may be provided via the mobile device to the user, such as, for example, coupon offers, offers for different levels of rewards and the like.

In some embodiments, the mobile communication device is configured to present MCRI related to medical first aid. The mobile communication device captures one or more images of a wound or other injury or illness. An artificial intelligence engine, running on either the mobile communication device and/or a server, determines the nature of the wound or other injury and searches for and/or retrieves information related to the proper first aid treatment for the wound or injury. For example, if a user has a cut on her hand, she can direct the mobile communication device to capture a video and/or still shot of the cut. The AI engine then determines that the wound is a cut and retrieves MCRI related to the proper first aid treatment for a cut. In some embodiments, the AI engine determines the size, shape, depth, location relative to the body and other information based on an analysis of the video and/or still shots. Based on the results of the analysis, the AI engine, in some embodiments, accesses a database including information related to proper treatment for a variety of injuries and/or illnesses. In some embodiments, the AI engine provides an automatic connection with a physician, nurse or other specialist using the mobile communication device. For example, the connection may be a telephone call, a text message, an email, an automated injury or illness audio and/or video message, and the like. In some embodiments, the AI engine forwards a video and/or still shots of the injury or evidence of illness, which in some embodiments, is done in conjunction with another connection, such as a telephone call.

In some embodiments, the mobile device and/or financial institution server(s) may be provided with a wish list from a user or administrator defined with predefined rules engines including instructions, such that when an offer, such as a targeted offer, or a product recognized for sale matches the predefined rules, the financial institution server(s) may execute purchase of and payment for the product on behalf of the user.

Thus, methods, systems, computer programs and the like have been disclosed that provide for using real-time video analysis and AR or the like to assist the user of mobile devices with commerce activities. Through the use real-time vision object recognition objects, logos, artwork, products, locations and other features that can be recognized in the real-time video stream can be matched to data associated with such to assist the user with commerce activity. The commerce activity may include, but is not limited to; conducting a transaction, providing information about a product/service, providing rewards based information, providing user-specific offers, or the like. In specific embodiments, the data that matched to the images in the real-time video stream in specific to financial institutions, such as customer financial behavior history, customer purchase power/transaction history and the like. In this regard, many of the embodiments herein disclosed leverage financial institution data, which is uniquely specific to financial institution, in providing information to mobile devices users in connection with real-time video stream analysis.

While the foregoing disclosure discusses illustrative embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any embodiment may be utilized with all or a portion of any other embodiment, unless stated otherwise.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

The systems, methods, computer program products, etc. described herein, may be utilized or combined with any other suitable AR-related application. Non-limiting examples of other suitable AR-related applications include those described in the following U.S. Provisional Patent Applications, the entirety of each of which is incorporated herein by reference:

| U.S. Provisional Ser. No. | Filed On | Title |
|---|---|---|
| 61/450,213 | Mar. 8, 2011 | Real-Time Video Image Analysis Applications for Commerce Activity |
| 61/478,409 | Apr. 22, 2011 | Presenting Offers on a Mobile Communication Device |
| 61/478,412 | Apr. 22, 2011 | Real-Time Video Analysis for Reward Offers |
| 61/478,394 | Apr. 22, 2011 | Real-Time Video Image Analysis for Providing Targeted Offers |
| 61/478,399 | Apr. 22, 2011 | Real-Time Analysis Involving Real Estate Listings |
| 61/478,402 | Apr. 22, 2011 | Real-Time Video Image Analysis for an Appropriate Payment Account |
| 61/478,405 | Apr. 22, 2011 | Presenting Investment-Related Information on a Mobile Communication Device |
| 61/478,393 | Apr. 22, 2011 | Real-Time Image Analysis for Medical Savings Plans |
| 61/478,397 | Apr. 22, 2011 | Providing Data Associated With Relationships Between Individuals and Images |
| 61/478,408 | Apr. 22, 2011 | Identifying Predetermined Objects in a Video Stream Captured by a Mobile Device |
| 61/478,400 | Apr. 22, 2011 | Real-Time Image Analysis for Providing Health Related Information |
| 61/478,411 | Apr. 22, 2011 | Retrieving Product Information From Embedded Sensors Via Mobile Device Video Analysis |
| 61/478,403 | Apr. 22, 2011 | Providing Social Impact Information Associated With Identified Products or Businesses |
| 61/478,407 | Apr. 22, 2011 | Providing Information Associated With an Identified Representation of an Object |
| 61/478,415 | Apr. 22, 2011 | Providing Location Identification of Associated Individuals Based on Identifying the Individuals in Conjunction With a Live Video Stream |
| 61/478,419 | Apr. 22, 2011 | Vehicle Recognition |
| 61/478,417 | Apr. 22, 2011 | Collective Network of Augmented Reality Users |
| 61/508,946 | Jul. 18, 2011 | Dynamically Identifying Individuals From a Captured Image |
| 61/508,980 | Jul. 18, 2011 | Providing Affinity Program Information |
| 61/508,821 | Jul. 18, 2011 | Providing Information Regarding Sports Movements |
| 61/508,850 | Jul. 18, 2011 | Assessing Environmental Characteristics in a Video Stream Captured by a Mobile Device |
| 61/508,966 | Jul. 18, 2011 | Real-Time Video Image Analysis for Providing Virtual Landscaping |
| 61/508,969 | Jul. 18, 2011 | Real-Time Video Image Analysis for Providing Virtual Interior Design |
| 61/508,971 | Jul. 18, 2011 | Real-Time Video Image Analysis for Providing Deepening Customer Value |
| 61/508,764 | Jul. 18, 2011 | Conducting Financial Transactions Based on Identification of Individuals in an Augmented Reality Environment |
| 61/508,973 | Jul. 18, 2011 | Real-Time Video Image Analysis for Providing Security |
| 61/508,976 | Jul. 18, 2011 | Providing Retail Shopping Assistance |
| 61/508,944 | Jul. 18, 2011 | Recognizing Financial Document Images |

What is claimed is:

1. A method for providing medical condition related information, the method comprising:

identifying, via a computing device processor, which objects in an image captured on a mobile communication device correspond to a medical condition based at least in part on global positioning system information associated with the mobile communication device or other information indicating a location of the mobile communication device;

determining, via a computing device processor, which of one or more medical conditions identified in the image video stream have associated medical condition related information; and presenting, via a display of the image on the mobile communication device, one or more medical condition related information indicators, each medical condition related information indicator presented proximate a location of the one or more medical conditions determined to have associated medical condition related information.

2. The method of claim 1, wherein identifying a medical condition comprises identifying one or more images in a video stream captured on a mobile communication device that correspond to one or more medical conditions.

3. The method of claim 1, wherein identifying a medical condition comprises identifying one or more objects in a still image captured on a mobile communication device that corresponds to one or more medical conditions.

4. The method of claim 1, wherein the medical condition related information comprises information related to the medical condition comprising information regarding proper treatment of the medical condition.

5. The method of claim 1, wherein determining which of the identified medical conditions have associated medical condition related information comprises comparing the identified medical conditions to a database listing of medical conditions currently associated with medical condition related information.

6. An apparatus for providing medical condition related information, the apparatus comprising:

a computing platform having a processor, a memory in communication with the processor, and image capture logic stored in the memory, executable by the processor and configured to capture an image, and medical condition identification logic stored in the memory, executable by the processor and configured to identify which objects in the image captured by a mobile communication device correspond to a medical condition based at least in part on global positioning system information associated with the mobile communication device or other information indicating a location of the mobile communication device, and medical condition related information logic stored in the memory, executable by the processor and configured to determine whether the identified medical condition has associated medical condition related information; and medical condition related information presentation logic stored in the memory, executable by the processor and configured to present, on a display of the mobile communication device, one or more medical condition related information indicators, each medical condition related information indicator presented proximate a location of the medical condition determined to have associated medical condition related information.

7. The apparatus of claim 6, wherein the medical condition identification logic is configured to identify one or more images in a video stream captured on a mobile communication device that correspond to one or more medical conditions.

8. The apparatus of claim 6, wherein the medical condition identification logic is configured to identify one or more objects in a still image captured on a mobile communication device that corresponds to one or more medical conditions.

9. The apparatus of claim 6, wherein the medical condition related information comprises information related to the medical condition comprising information regarding proper treatment of the medical condition.

10. The apparatus of claim 6, wherein the medical condition related information logic is configured to determine which of the identified medical conditions have associated medical condition related information comprises comparing the identified medical conditions to a database listing of medical conditions currently associated with medical condition related information.

11. A computer program product comprising a non-transitory computer-readable medium comprising computer-executable instructions for providing health related information, the instructions comprising:
   instructions for identifying which objects in an image captured on a mobile communication device correspond to a medical condition based at least in part on global positioning system information associated with the mobile communication device or other information indicating a location of the mobile communication device;
   instructions for determining which of one or more medical conditions identified in the image have associated medical condition related information; and
   instructions for presenting one or more medical conditions related information indicators with an image displayed on the mobile communication device, each medical condition related information indicator presented proximate a location of the one or more determined medical conditions.

12. A method for providing medical condition related information, the method comprising:
   identifying, via a server in communication with a mobile communication device, which objects in an image captured on a mobile communication device correspond to a medical condition based at least in part on global positioning system information associated with the mobile communication device or other information indicating a location of the mobile communication device;
   determining, via the server, which of one or more medical conditions identified in the image have associated medical condition related information; and
   communicating instructions to the mobile communication device, via the server, for presenting a display of the image on the mobile communication device, one or more medical condition related information indicators, each medical condition related information indicator presented proximate a location of the one or more medical conditions determined to have associated medical condition related information.

13. The method of claim 12, wherein identifying a medical condition comprises identifying one or more images in a video stream captured on a mobile communication device that correspond to one or more medical conditions.

14. The method of claim 12, wherein identifying a medical condition comprises identifying one or more objects in a still image captured on a mobile communication device that corresponds to one or more medical conditions.

15. The method of claim 12, wherein the medical condition related information comprises information related to the medical condition comprising information regarding proper treatment of the medical condition.

16. The method of claim 12, wherein determining which of the identified medical conditions have associated medical condition related information comprises comparing the identified medical conditions to a database listing of medical conditions currently associated with medical condition related information.

17. An apparatus for providing medical condition related information, the apparatus comprising:
   a server having a processor, a memory in communication with the processor, and communication logic stored in the memory, executable by the processor and configured to receive data from a mobile communication device, the data corresponding to one or more objects in an image captured by the mobile communication device;
   medical condition identification logic stored in the memory, executable by the processor and configured to identify which objects in the image captured by the mobile communication device correspond to a medical condition based at least in part on global positioning system information associated with the mobile communication device or other information indicating a location of the mobile communication device;
   medical condition related information logic stored in the memory, executable by the processor and configured to determine whether the identified medical condition has associated medical condition related information; and
   medical condition related information presentation logic stored in the memory, executable by the processor and configured to communicate instructions for presenting, on a display of the mobile communication device, one or more medical condition related information indicators, each medical condition related information indicator presented proximate a location of the medical condition determined to have associated medical condition related information.

18. The apparatus of claim 17, wherein the medical condition identification logic is configured to identify one or more images in a video stream captured on a mobile communication device that correspond to one or more medical conditions.

19. The apparatus of claim 17, wherein the medical condition identification logic is configured to identify one or more objects in a still image captured on a mobile communication device that corresponds to one or more medical conditions.

20. The apparatus of claim 17, wherein the medical condition related information comprises information related to the medical condition comprising information regarding proper treatment of the medical condition.

21. The apparatus of claim 17, wherein the medical condition related information logic is configured to compare the identified medical conditions to a database listing of medical conditions currently associated with medical condition related information.

22. A computer program product comprising a non-transitory computer-readable medium comprising computer-executable instructions for execution on a server in communication with a mobile communication device, the instructions for providing medical condition related information, the instructions comprising:
   instructions for identifying which objects in an image captured on a mobile communication device correspond to a medical condition based at least in part on global positioning system information associated with the mobile communication device or other information indicating a location of the mobile communication device;
   instructions for determining which of one or more medical conditions identified in the image have associated medical condition related information; and
   instructions for communicating instructions to the mobile communication device for presenting one or more medical condition related information indicators with the image displayed on the mobile communication device, each medical condition related information indicator presented proximate a location of the one or more determined medical conditions.

23. A method for providing medical condition information, the method comprising:
   identifying, via a computing device processor, which objects in an image captured on a mobile communication device correspond to a product based at least in part on global positioning system information associated with the mobile communication device or other information indicating a location of the mobile communication device;
   determining, via a computing device processor, which of one or more products identified in the image are associated with treatment of a previously identified medical condition; and
   presenting, via a display of the live video stream on the mobile communication device, one or more medical condition indicators, each medical condition indicator presented proximate a location of the one or more products determined to be associated with treatment of the previously identified medical condition.

24. The method of 23, wherein the medical condition related information comprises at least one of nutrition information, caloric information, medical indication information, proper medicinal treatment information, or financial impact information.

25. The method of claim 23, wherein determining which of the identified products have associated medical condition related information comprises comparing the identified products to a database listing of products currently associated with medical condition related information.

26. The method claim 23, further comprising:
   storing information related to at least one medical or health need or want of a social network member of a user of the mobile communication device;
   determining whether any of the identified products meet the health need or want of the social network member; and
   presenting at least one health related information indicator indicating that at least one identified product meets the health need or want of the social network member.

27. The method of claim 23, further comprising:
   storing information related to at least one medical or health characteristic of a user of the mobile communication device;
   determining whether any of the identified products effect the health characteristic of the user; and
   presenting at least one health related information indicator indicating that at least one identified product effects the health characteristic of the user.

28. An apparatus for providing medical condition information, the apparatus comprising:
   a computing platform having a processor, a memory in communication with the processor, and
   image capture logic stored in the memory, executable by the processor and configured to capture an image, and
   product identification logic stored in the memory, executable by the processor and configured to identify which objects in the image captured by a mobile communication device correspond to a product based at least in part on global positioning system information associated with the mobile communication device or other information indicating a location of the mobile communication device, and
   medical condition related information logic stored in the memory, executable by the processor and configured to determine whether the identified product is associated with treatment of a previously identified medical condition; and
   medical condition related information presentation logic stored in the memory, executable by the processor and configured to present, on a display of the mobile communication device, one or more medical condition related information indicators, each medical condition related information indicator presented proximate a location of the product determined to be associated with treatment of the previously identified medical condition.

* * * * *